United States Patent
Nussbaum et al.

(10) Patent No.: US 10,662,225 B2
(45) Date of Patent: May 26, 2020

(54) BACKBONE CYCLIZED INHIBITORY PEPTIDES OF MYELOID DIFFERENTIATION FACTOR 88 (MYD88)

(71) Applicant: Yissum Research Development Company of the Hebrew University of Jerusalem Ltd., Jerusalem (IL)

(72) Inventors: Gabriel Nussbaum, Jerusalem (IL); Amnon Hoffman, Jerusalem (IL); Chaim Gilon, Jerusalem (IL)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 0 days.

(21) Appl. No.: 16/307,841

(22) PCT Filed: Jun. 4, 2017

(86) PCT No.: PCT/IL2017/050621
§ 371 (c)(1),
(2) Date: Dec. 6, 2018

(87) PCT Pub. No.: WO2017/212477
PCT Pub. Date: Dec. 14, 2017

(65) Prior Publication Data
US 2019/0185516 A1 Jun. 20, 2019

Related U.S. Application Data

(60) Provisional application No. 62/346,580, filed on Jun. 7, 2016.

(51) Int. Cl.
| | |
|---|---|
| *C07K 7/56* | (2006.01) |
| *A61P 21/00* | (2006.01) |
| *A61P 35/00* | (2006.01) |
| *A61P 25/14* | (2006.01) |
| *A61P 37/08* | (2006.01) |
| *A61K 38/00* | (2006.01) |

(52) U.S. Cl.
CPC .............. *C07K 7/56* (2013.01); *A61P 21/00* (2018.01); *A61P 25/14* (2018.01); *A61P 35/00* (2018.01); *A61P 37/08* (2018.01); *A61K 38/00* (2013.01)

(58) Field of Classification Search
CPC ............. A61P 35/00; A61P 21/00; C07K 7/56
See application file for complete search history.

(56) References Cited

U.S. PATENT DOCUMENTS

| | | | |
|---|---|---|---|
| 5,811,392 | A | 9/1998 | Gilon |
| 5,874,529 | A | 2/1999 | Gilon |
| 5,883,293 | A | 3/1999 | Gilon |
| 6,051,554 | A | 4/2000 | Hornik |
| 6,117,974 | A | 9/2000 | Gilon |
| 6,265,375 | B1 | 7/2001 | Gilon |
| 6,355,613 | B1 | 3/2002 | Hornik |
| 6,407,059 | B1 | 6/2002 | Gilon |
| 6,512,092 | B2 | 1/2003 | Falb |
| 2008/0064643 | A1 | 3/2008 | Carminati |

FOREIGN PATENT DOCUMENTS

| | | |
|---|---|---|
| WO | 95/33765 A1 | 12/1995 |
| WO | 97/09344 A2 | 3/1997 |
| WO | 98/04583 A1 | 2/1998 |
| WO | 99/31121 A2 | 6/1999 |
| WO | 99/65508 A1 | 12/1999 |
| WO | 00/02898 A1 | 1/2000 |
| WO | 00/65467 A1 | 11/2000 |
| WO | 02/062819 A2 | 8/2002 |
| WO | 2013/012806 A2 | 1/2013 |
| WO | 2013/111129 A1 | 8/2013 |
| WO | 2014/130949 A1 | 8/2014 |

OTHER PUBLICATIONS

Bartfai et al., (2003) A low molecular weight mimic of the Toll/IL-1 receptor/resistance domain inhibits IL-1 receptor-mediated responses. Proc Natl Aced Sci U S A 100(13): 7971-7976.
Cohen et al., (2010) IL-10 mediates resistance to adoptive transfer experimental autoimmune encephalomyelitis in MyD88(-/-) mice. J Immunol 184(1): 212-221.
Compston et al., (2008) Multiple sclerosis. Lancet 372(9648): 1502-1517.
Dishon et al., (2017) Inhibition of Myeloid Differentiation Factor 88 Reduces Human and Mouse T-Cell Interleukin-17 and IFNγ Production and Ameliorates Experimental Autoimmune Encephalomyelitis Induced in Mice. Front Immunol 8: 615; 12 pages.
Fanto et al., (2008) Design, synthesis, and in vitro activity of peptidomimetic inhibitors of myeloid differentiation factor 88. J Med Chem 51(5): 1189-1202.
Gazal et al., (2002) Human somatostatin receptor specificity of backbone-cyclic analogues containing novel sulfur building units. J Med Chem 45(8): 1665-1671.
Hayouka et al., (2010) Cyclic peptide inhibitors of HIV-1 integrase derived from the LEDGF/p75 protein. Bioorg Med Chem 18(23): 8388-8395.
Hess et al., (2008) Backbone cyclic peptidomimetic melanocortin-4 receptor agonist as a novel orally administrated drug lead for treating obesity. J Med Chem 51(4): 1026-1034.
Hines et al., (2013) Prevention of LPS-induced microglia activation, cytokine production and sickness behavior with TLR4 receptor interfering peptides. PLoS One 8(3):e60388; 10 pages.
Hurevich et al., (2010) Rational conversion of noncontinuous active region in proteins into a small orally bioavailable macrocyclic drug-like molecule: the HIV-1 CD4:gp120 paradigm. Bioorg Med Chem 18(15): 5754-5761.

(Continued)

*Primary Examiner* — James H Alstrum-Acevedo
*Assistant Examiner* — Kaipeen E Yang
(74) *Attorney, Agent, or Firm* — J.A. Lindeman & Co., PLLC

(57) ABSTRACT

Provided are backbone cyclized peptides that interfere with signaling of the intracellular adaptor protein MyD88. Pharmaceutical compositions including these backbone cyclized peptides as well as their use in treatment of multiple sclerosis (MS) and other diseases associated with MyD88 signaling are also disclosed.

9 Claims, 15 Drawing Sheets

Specification includes a Sequence Listing.

(56) References Cited

OTHER PUBLICATIONS

Kfoury et al., (2014) Dual function of MyD88 in inflammation and oncogenesis: implications for therapeutic intervention. Curr Opin Oncol 26(1): 86-91.

Lambert et al., (2001) The synthesis of cyclic peptides. J Chem Soc Perkin Trans 1: 471-484.

Loiarro et al., (2005) Peptide-mediated interference of TIR domain dimerization in MyD88 inhibits interleukin-1-dependent activation of NF-{kappa}B. J Biol Chem 280(16): 15809-15814.

Loiarro et al., (2007) Pivotal Advance: Inhibition of MyD88 dimerization and recruitment of IRAK1 and IRAK4 by a novel peptidomimetic compound. J Leukoc Biol 82(4): 801-810.

Loiarro et al., (2010) Targeting TLR/IL-1R signalling in human diseases. Mediators Inflamm 2010: 674363; 12 pages.

Miranda-Hernandez et al., (2013) Role of toll-like receptors in multiple sclerosis. Am J Clin Exp Immunol 2(1): 75-93.

Ngo et al., (2011) Oncogenically active MYD88 mutations in human lymphoma. Nature 470(7332): 115-119.

Olson et al., (2015) Discovery of small molecule inhibitors of MyD88-dependent signaling pathways using a computational screen. Sci Rep 5: 14246; 14 pages.

Owens et al., (1995) The immunology of multiple sclerosis and its animal model, experimental allergic encephalomyelitis. Neurol Clin 13(1): 51-73.

Pillai et al., (2001) Polymers in drug delivery. Curr Opin Chem Biol 5(4): 447-451.

Prinz et al., (2006) Innate immunity mediated by TLR9 modulates pathogenicity in an animal model of multiple sclerosis. J Clin Invest 116(2): 456-464.

Rosenberg, (2007) Rational design of MyD88 inhibitors-new pathways to inflammatory control: an interview with Dr. Claudio Sette. J Leukoc Biol 82(4): 811-812.

Salcedo et al., (2013) MyD88 and its divergent toll in carcinogenesis. Trends Immunol 34(8): 379-389.

Van Tassell et al., (2010) Pharmacologic inhibition of myeloid differentiation factor 88 (MYD88) prevents left ventricular dilation and hypertrophy after experimental acute myocardial infarction in the mouse. J Cardiovasc Pharmacol 55(4): 385-390.

Xu et al., (2013) MYD88 L265P in Waldenström macroglobulinemia, immunoglobulin M monoclonal gammopathy, and other B-cell lymphoproliferative disorders using conventional and quantitative allele-specific polymerase chain reaction. Blood 121(11): 2051-2058. With erratum.

Yang et al., (2013) A mutation in MYD88 (L265P) supports the survival of lymphoplasmacytic cells by activation of Bruton tyrosine kinase in Waldenström macroglobulinemia. Blood 122(7): 1222-1232.

Byk et al., (1996) Synthesis and biological activity of NK-1 selective, N-backbone cyclic analogs of the C-terminal hexapeptide of substance P. J Med Chem 39(16): 3174-3178.

Humphrey and Chamberlin (1997) Chemical Synthesis of Natural Product Peptides: Coupling Methods for the Incorporation of Noncoded Amino Acids into Peptides. Chem Rev 97(6): 2243-2266.

SEQUENCE LISTING

```
<160> NUMBER OF SEQ ID NOS: 8

<210> SEQ ID NO 1
<211> LENGTH: 7
<212> TYPE: PRT
<213> ORGANISM: Artificial Sequence
<220> FEATURE:
<223> OTHER INFORMATION: synthetic peptide

<400> SEQUENCE: 1

Arg Asp Val Leu Pro Gly Thr
1               5

<210> SEQ ID NO 2
<211> LENGTH: 4
<212> TYPE: PRT
<213> ORGANISM: Artificial Sequence
<220> FEATURE:
<223> OTHER INFORMATION: synthetic peptide

<400> SEQUENCE: 2

Arg Asp Val Leu
1

<210> SEQ ID NO 3
<211> LENGTH: 146
<212> TYPE: PRT
<213> ORGANISM: Homo sapiens

<400> SEQUENCE: 3

Asp Asp Pro Leu Gly His Met Pro Glu Arg Phe Asp Ala Phe Ile Cys
1               5                   10                  15

Tyr Cys Pro Ser Asp Ile Gln Phe Val Gln Glu Met Ile Arg Gln Leu
                20                  25                  30

Glu Gln Thr Asn Tyr Arg Leu Lys Leu Cys Val Ser Asp Arg Asp Val
            35                  40                  45

Leu Pro Gly Thr Cys Val Trp Ser Ile Ala Ser Glu Leu Ile Glu Lys
        50                  55                  60
```

```
Arg Cys Arg Arg Met Val Val Val Ser Asp Asp Tyr Leu Gln Ser
 65                  70                  75                  80

Lys Glu Cys Asp Phe Gln Thr Lys Phe Ala Leu Ser Leu Ser Pro Gly
                 85                  90                  95

Ala His Gln Lys Arg Leu Ile Pro Ile Lys Tyr Lys Ala Met Lys Lys
            100                 105                 110

Glu Phe Pro Ser Ile Leu Arg Phe Ile Thr Val Cys Asp Tyr Thr Asn
        115                 120                 125

Pro Cys Thr Lys Ser Trp Phe Trp Thr Arg Leu Ala Lys Ala Leu Ser
    130                 135                 140

Leu Pro
145

<210> SEQ ID NO 4
<211> LENGTH: 21
<212> TYPE: PRT
<213> ORGANISM: Mus musculus

<400> SEQUENCE: 4

Met Glu Val Gly Trp Tyr Arg Ser Pro Phe Ser Arg Val Val His Leu
1               5                   10                  15

Tyr Arg Asn Gly Lys
            20

<210> SEQ ID NO 5
<211> LENGTH: 7
<212> TYPE: PRT
<213> ORGANISM: Artificial Sequence
<220> FEATURE:
<223> OTHER INFORMATION: synthetic peptide

<400> SEQUENCE: 5

Pro Thr Asp Leu Val Arg Gly
1               5

<210> SEQ ID NO 6
<211> LENGTH: 9
<212> TYPE: PRT
<213> ORGANISM: Artificial Sequence
<220> FEATURE:
<223> OTHER INFORMATION: synthetic
<220> FEATURE:
<221> NAME/KEY: VARIANT
<222> LOCATION: (1)..(1)
<223> OTHER INFORMATION: Xaa is selected from an hydrogen, an aromatic
      amino acid residue and a permeability enhancing moiety
<220> FEATURE:
<221> NAME/KEY: MOD_RES
<222> LOCATION: (2)..(2)
<223> OTHER INFORMATION: Xaa is a N-alpha-functionalized amino acid
<220> FEATURE:
<221> NAME/KEY: BINDING
<222> LOCATION: (2)..(7)
<223> OTHER INFORMATION: Modified residue 2 and modified residue 7 are
      covalently conected to form a backbone cyclized peptide
<220> FEATURE:
<221> NAME/KEY: MOD_RES
<222> LOCATION: (7)..(7)
<223> OTHER INFORMATION: Xaa is a N-alpha-functionalized amino acid

<400> SEQUENCE: 6

Xaa Xaa Arg Asp Val Leu Xaa Gly Thr
1               5

<210> SEQ ID NO 7
```

```
<211> LENGTH: 25
<212> TYPE: DNA
<213> ORGANISM: Homo sapiens

<400> SEQUENCE: 7
gggatatgct gaactaagtt gccac                                      25

<210> SEQ ID NO 8
<211> LENGTH: 25
<212> TYPE: DNA
<213> ORGANISM: Homo sapiens

<400> SEQUENCE: 8
gacgtgtctg tgaagttggc atctc                                      25
```

BACKBONE CYCLIZED INHIBITORY PEPTIDES OF MYELOID DIFFERENTIATION FACTOR 88 (MYD88)

SEQUENCE LISTING

The Sequence Listing submitted in text format (.txt) filed on Dec. 6, 2018, named "SequenceListing.txt", created on Nov. 26, 2018 (2.37 KB), is incorporated herein by reference.

FIELD OF THE INVENTION

The present invention is in the fields of immunology and peptide biochemistry and relates to inhibition of the activity of the intracellular adaptor protein myeloid differentiation factor 88 (MyD88) by backbone cyclized peptides. The present invention further relates to pharmaceutical compositions comprising these cyclic peptides, and methods for using them in treatment of multiple sclerosis and other diseases and disorders associated with MyD88 signaling, activation and dimerization.

BACKGROUND OF THE INVENTION

Myeloid differentiation factor 88 (MyD88) recruits signaling proteins to the intracellular domain of receptors belonging to the Toll-like/Interleukin-1 receptor (TIR) superfamily. MyD88 plays a crucial role in the transduction events triggered by all toll-like receptors (TLR), except TLR3, as well as the family of IL-1 receptors (such as the IL-1 receptor and IL-18 receptor). Therefore, inhibition of this adaptor protein, involved in the activation of NF-kB, triggered by signals from receptors that recognize distinct ligands but share the same transduction pathway, is expected to be more effective than inhibition of the individual ligand activities.

There is a consensus that MyD88-dependent signaling contributes to Experimental Autoimmune Encephalomyelitis (EAE), the animal model of multiple sclerosis (Socorro Miranda-Hernandez and Alan G Baxter, Am J Clin Exp Immunol. 2013; 2(1): 75-93). Mice lacking MyD88 are highly susceptible to infectious diseases, but they are for the most part resistant to experimentally-induced autoimmune diseases such as EAE. MyD88 deficient mice are not only resistant to EAE induced by active immunization against CNS antigens, but also to EAE induced by passive transfer of previously activated encephalitogenic wild-type (WT) T cells (Cohen et al., J Immunol., 2010, 184).

There is also evidence that activating mutations in MyD88 are common in subtypes of lymphoma. Furthermore, strong preclinical evidence suggests that MyD88 drives oncogenesis through inflammatory and non-inflammatory pathways (Salcedo et al, Trends in Immunology 2013 34(8):379-389; Ngo et al Nature 2011, 470:115-119, 3. Yang et al, Blood 2013 122(7):1222-1232).

The MyD88 function is dependent on homodimerization (MyD88-MyD88) and heterodimerization (MyD88-TLR, MyD88-cytokine receptor, or MyD88-kinase). Multiple MyD88 molecules then form a protein complex (termed the "Myddosome") that is critical for recruitment of downstream kinases and their phosphorylation. The crystal structure of MyD88 TIR domain revealed a loop between the second beta strand and the second alpha helix (the "BB loop") that mediates dimerization (Loiarrio et al., J. Biol Chem 2005, 280, 16, 15809-15814). The BB loop heptapeptide having the sequence RDVLPGT (SEQ ID NO: 1), that correlates to this region, competitively inhibits dimerization.

Several small molecule inhibitors of MyD88 are known. Bartfai et al., PNAS 2003, 100, 13, 7971-7976 reported a low molecular weight MyD88 mimetic, hydrocinnamoyl-L-valyl pyrrolidone, modeled on a tripeptide sequence of the BB-loop of the TIR domain. The compound interferes with the interaction between mouse MyD88 and IL-1RI.

Fanto et al., J. Med. Chem 2008, 51, 1189-1202 describe the design, synthesis and in-vitro activity of peptidomimetic inhibitors of MyD88 which also interfere with MyD88 dimerization. The small molecules described comprise a beta turn mimetic and an arginine mimetic connected by a spacer.

Olson et al., Nature (Scientific Reports 5, Article number: 14246, 2015), discovered small molecule inhibitors of MyD88-dependent signaling pathways using a computational screen. The best compounds inhibit cytokine secretion at micromolar range in human cells and protect mice from septic shock.

Van Tassell et al., J Cardiovasc Pharmacol. 2010 55(4): 385-90 have showed that inhibition of MyD88 prevents left ventricular dilation and hypertrophy after experimental acute myocardial infarction in the mouse and suggests that MyD88 may be a viable target for pharmacologic inhibition in acute myocardial infarction.

US20080064643 discloses non-natural peptides and peptidomimetic of the 7 amino acids linear BB loop peptide.

Autoimmune diseases are characterized by over-abundant inflammation. Multiple sclerosis is an autoimmune inflammatory demyelinating disease of the central nervous system (CNS). MS affects mainly young adults and it is the leading cause of neurological disability in this age group. The course of the MS is either relapsing and remitting or progressive. During the relapses of the disease, autoimmune, anti-myelin reactive lymphocytes are produced, activated and recruited from the peripheral immune system, enter the CNS and attack the myelin components, inducing neurological deficits which depend on the area of the white matter of the CNS that is affected each time (i.e. loss of vision, motor paralysis, instability of gait, problems in coordination of movements, loss of sphincters control, sensory disturbances etc). Despite dramatic improvement during the last decades, in the diagnostic tools for MS (basically due to the widespread availability of brain and spinal MRI), understanding of the basic etiology of the disease remains limited. Fully effective control of the disease activity and progression and the repair of damaged myelin are key objectives for current and future investigators. Based on the widely accepted autoimmune pathogenetic model, the current treatment options for MS include various modalities that downregulate or modulate the inflammatory process and the immune anti-myelin responses. Acute attacks (relapses) of MS are typically treated with glucocorticoids. Patients with relapsing-remitting MS who have current disease activity manifested by clinical symptoms or active new MRI lesions are treated with other, long-term acting, immunomodulatory drugs, such as interferon beta (Avonex®, Rebif®, Betaseron®), glatiramer acetate (Copaxone®), fingolimod and the chemotherapeutic agent mitoxanthrone (Compston, A.; Coles, A., Multiple sclerosis. Lancet 2008, 372, (9648), 1502-17). Almost all of these drugs are administered with injections and are associated with various adverse effects which both limit their ease of use for long periods of time. In addition, all of these treatments are partially effective and can only reduce the relapse and progression rates of MS by approximately 30%.

Backbone cyclization (BC) was already proved to be a valuable tool in methodological conversion of active sites of proteins to cyclic peptides and even to small macrocycles (Hurevich et al., Bioorg Med Chem 2010, 18, (15), 5754-5761; Hayouka et al., Bioorg Med Chem 2010, 18, (23), 8388-8395; Hess et al., J Med Chem 2008, 51, (4), 1026-34). The BC method is used to introduce global constraints to active peptides. It differs from other cyclization methods since it utilizes non-natural building blocks for cycle anchors, mainly N-alkylated amino acids. BC proved superior to other stabilization methods since the resultant peptides had defined structures that led to better selectivity (Gazal et al., J Med Chem 2002, 45, (8), 1665-71; WO 99/65508) and improved pharmacological properties. The use of BC enables a combinatorial approach called "cycloscan". It was used for generating and screening BC peptide libraries to find lead peptides that overlap with the bioactive conformation. In a cycloscan, all the peptides in the library bear the same sequence but differ from each other in other parameters that constraint the conformational space. Screening the library allows an iterative evaluation of the effect of chemical modifications on the structural properties and biological function. Changing the ring size and ring chemistry proved to be the most convenient modification to perform in cycloscan and has been used to synthesize small- and medium-sized peptide libraries. However, obtaining an active cyclic analog based on a linear sequence is not a straightforward process.

No cure exists for MS and there is a strong need for additional disease modifying therapies as many patients continue to worsen on currently available treatments. There is an unmet need for metabolically stable, tissue permeable, preferably orally bioavailable and more effective therapeutic modalities for MS.

SUMMARY OF THE INVENTION

The present invention provides backbone cyclized compounds designed to serve as effective, metabolically stable and permeable mimetics of a loop peptide from TIR domain of the adaptor protein MyD88. These novel compounds are capable of inhibiting the activity of the MyD88. The present invention further provides pharmaceutical compositions and methods of treating conditions associated with signaling through the MyD88 adaptor protein, such as inflammatory and autoimmune diseases and in particular multiple sclerosis.

Without wishing to be bound to any theory of mechanism of action, it is suggested that some of the compounds of the present invention are capable of inhibiting homodimerization of MyD88, or heterodimerization, namely binding of MyD88 to Toll receptor or cytokine receptor.

While linear peptides and small molecule mimetics of the loop peptide from MyD88 are known, the backbone cyclic peptide analogs of the present invention not only resemble more precisely and to a greater extent, the native protein segment, they were also proved to be metabolically stable and tissue permeable, therefore suitable for oral or parenteral administration. The uniqueness of the backbone cyclic peptide approach provides both utilization of the right sequence in its specific active conformation while preventing peptidases from the biological fluids in the surrounding vicinity to degrade these compounds. The size and chemistry of the bridge is the key for obtaining these achievements of the novel molecules.

The present invention provides, according to one aspect, a backbone cyclic peptide analog of the peptide Arg-Asp-Val-Leu-Pro-Gly-Thr (RDVLPGT, SEQ ID NO: 1), wherein the backbone cyclic analog comprises at least three contiguous amino acids derived from SEQ ID NO: 1 or from an analog thereof comprising conservative substitutions; at least one $N_\alpha$-ω-functionalized derivative of amino acid residue (building unit, BU) connected to a second building unit, to a side chain or to a free terminal of the peptide to form a cyclic peptide; and an optional permeability enhancing moiety.

A backbone cyclic peptide is therefore provided comprising at least three contiguous amino acids from SEQ ID NO: 1; at least one $N_\alpha$-ω-functionalized derivative of amino acid residue (building unit, BU) connected to a second BU, to a side chain or to a free terminal of the peptide, to form a cyclic peptide; and an optional permeability enhancing moiety and an optional modified peptide terminal.

According to some embodiments, the backbone cyclic peptide analog consists of 5-12 amino acids and an optional permeability enhancing moiety. According to other embodiments, the backbone cyclic peptide analog consists of 6-10 amino acids and an optional permeability enhancing moiety. Each possibility represents a separate embodiment of the present invention.

Peptide analogs according to the present invention form a cyclic structure by connecting two amino acid residues of the sequence, using a backbone cyclization, namely, covalently connecting at least one amino acid residue in the peptide sequence, which was substituted with a $N^\alpha$-ω-functionalized or an $C^\alpha$-ω-functionalized derivative of amino acid residue (herein after, Building unit, BU), with a moiety selected from the group consisting of: another $N^\alpha$-ω-functionalized or an $C^\alpha$-ω-functionalized derivative of amino acid residue, with the side chain of an amino acid in the peptide sequence, or with one of the peptide terminals, to form a backbone cyclic peptide.

A building unit (BU) according to some embodiments of the invention designates a $N^\alpha$-ω-functionalized amino acid residue (N-BU) of the formula:

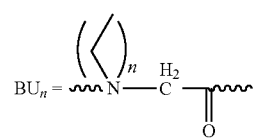

Formula I

According to some embodiments, the peptide sequence is cyclized by covalently connecting one $N^\alpha$-ω-functionalized derivative of amino acid residue added to the sequence, or substituted an amino acid residue in the sequence, with another $N^\alpha$-ω-functionalized derivative of amino acid residue in the sequence.

According to some embodiments, the peptide comprises two $N^\alpha$-ω-functionalized Glycine residues (Gly BUs) cyclized via urea bond to form a backbone cyclic peptide.

Any covalent bond may be used to connect the anchoring positions of the peptide sequence using backbone cyclization. According to some embodiments, the building units are connected by a bond selected from the group consisting of: urea bond, thiourea bond, amide bond, disulfide bond and guanidino group, namely the cyclization bridge is selected from the group consisting of: urea bridge, thiourea bridge and guanidino bridge. According to some particular embodiments, the bond used for cyclization is a urea bond.

According to some embodiments, the backbone cyclic peptide comprises at least one modified terminal, including but not limited to an amidated C-terminus and an acylated N-terminus.

According to some embodiments, the backbone cyclic peptide analog consists of 6, 7 or 8 amino acids and an optional permeability enhancing moiety. Each possibility represents a separate embodiment of the present invention.

According to some specific embodiments, the backbone cyclic peptide comprises 4, 5 or 6 natural occurring amino acids and at least one functionalized derivative of an amino acid. Each possibility represents a separate embodiment of the present invention.

According to some embodiments, the backbone cyclic peptide analog comprises the sequence Arg-Asp-Val-Leu (RDVL, SEQ ID NO: 2) within the cyclized part of the peptide.

According to some embodiments, the backbone cyclic analog comprises 1-3 modification to SEQ ID NO: 1 said modifications are selected from the group consisting of: deletions of amino acids, substitutions of amino acids, additions of amino acids, and combinations thereof. Each possibility represents a separate embodiment of the present invention.

According to some embodiments, the backbone cyclic peptide analog comprises 1-2 additions, substitutions or deletions of amino acids, to SEQ ID NO: 1.

According to yet other embodiments, the at least one amino acid substitution is to a $N^\alpha$-ω-functionalized amino acid.

According to yet other embodiments, the at least one amino acid addition to SEQ ID NO: 1, is of a $N^\alpha$-ω-functionalized amino acid.

According to some embodiments the backbone cyclic peptide analog comprises the sequence RDVLX$_1$GT wherein X$_1$ designates a $N^\alpha$-ω-functionalized amino acid (BU).

According to some embodiments the backbone cyclic peptide analog is according to Formula II:

ZX$_2$RDVLX$_1$GT (Formula II; SEQ ID NO: 6)

wherein X$_1$ and X$_2$ each designates a $N^\alpha$-ω-functionalized amino acid, Z is selected from the group consisting of: an hydrogen, an aromatic amino acid residue and a permeability enhancing moiety, and X$_1$ and X$_2$ are connected via a covalent bond to form a bridge.

According to some embodiments the permeability enhancing moiety is selected from a fatty acid and a transporter peptide.

According to some embodiments, the fatty acid is a myristic acid.

According to some embodiments, the transporter peptide comprises a stretch of Arginine residues.

According to some embodiments the covalent bond connecting X$_1$ and X$_2$ to form a bridge is selected from the group consisting of: amide bond, disulfide bond, and urea bond. According to some particular embodiments, the bridging bond is a urea bond.

According to some specific embodiments, the backbone cyclized peptide analog is according to Formula III:

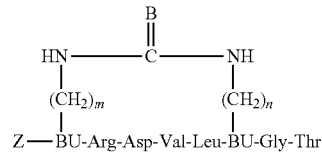

Formula III

Z—BU-Arg-Asp-Val-Leu-BU-Gly-Thr wherein m and n are each independently an integer of 2, 3, 4 or 6; B is selected from the group consisting of: O, S and NH; Z is selected from the group consisting of: hydrogen, Trp residue, and permeability enhancing moiety; and BU designates a $N^\alpha$-ω-functionalized amino acid residue. Each possibility represents a separate embodiment of the present invention.

According to some specific embodiments, m is 4 and n is 4.

According to some specific embodiments BU designates a $N^\alpha$-ω-functionalized Glycine residue.

According to other embodiments BU designates a $N^\alpha$-ω-functionalized residue of a natural or synthetic amino acid other than Glycine.

According to other embodiments, Z is a Trp residue, a fatty acid or (DArg)$_9$.

The moiety Z may be connected directly to the peptide sequence or, according to other embodiments, through a linker or spacer.

According to some embodiments, the backbone cyclized peptide is according to Formula IV:

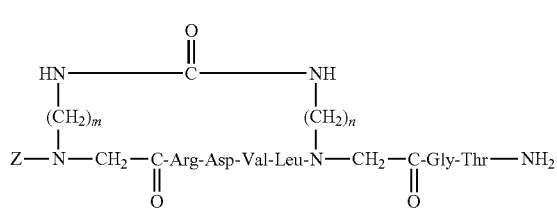

Formula IV wherein m and n each independently designates an integer selected from the group consisting of 2, 3, 4 and 6; and Z designates an hydrogen a Tryptophan residue, a myristic acid residue or (DArg)$_9$. Each possibility represents a separate embodiment of the present invention, namely a backbone cyclized peptide according to Formula IV is selected from the following possibilities: n=2, m=2; n=2, m=3; n=2, m=4; n=2, m=6; n=3, m=2; n=3, m=3; n=3, m=4; n=3, m=6; n=4, m=2; 4=2, m=3; 4=2, m=4; n=4, m=6; n=6, m=2; n=6, m=3; n=6, m=4; and n=6, m=6.

According to some specific embodiments, n=4. According to some other embodiments m=4. According to yet other embodiments, n=4 and m=4 and the backbone cyclic peptide is denoted 4×4MyDI.

According to some embodiments, the backbone cyclic peptide comprises a permeability enhancing moiety connected to the peptide directly or through a linker or spacer.

The permeability-enhancing moiety may be connected to any location of the peptide sequence. According to some specific embodiments, the permeability enhancing moiety is connected to the N-terminus of the peptide sequence. According to other embodiments, the permeability-enhancing moiety is part of the backbone cyclization bridge. Each possibility represents a separate embodiment of the present invention.

Any moiety known to actively or passively enhance or facilitate permeability of the peptide analogs can be used in conjugation with the backbone cyclic peptide analogs of the present invention. Non-limitative examples include: moieties which may have cell-membrane receptors or carriers, such as steroids, vitamins and sugars, natural and non-natural amino acids, fatty acids and transporter peptides. According to some embodiments, the moiety is a hydrophobic moiety or hydrophobic amino acid residue. According to some embodiments, the hydrophobic amino acid is a Tryptophan (Trp) residue. According to other embodiments, the moiety is a fatty acid. According to yet other embodiments, the moiety is a transporter peptide.

According to some embodiments, the transporter peptide is (DArg)$_9$.

According to some embodiments the fatty acid is myristyl and the backbone cyclic peptide is according to formula V:

Formula V $$CH_3-(CH_2)_{12}-CO-N(CH_2-CO-Arg-Asp-Val-Leu-N(CH_2-CO-Gly-Thr-NH_2)-(CH_2)_4-NH-C(=O)-NH-(CH_2)_4)$$

Myr-MYD4X4

Any other fatty acid may be conjugated with a backbone cyclic peptide of the invention to enhance its permeability.

According to other embodiments, the permeability enhancing moiety is a transport peptide. An exemplary transport peptide is (DArg)$_9$ and according to some embodiments, the backbone cyclic peptide is according to formula VI:

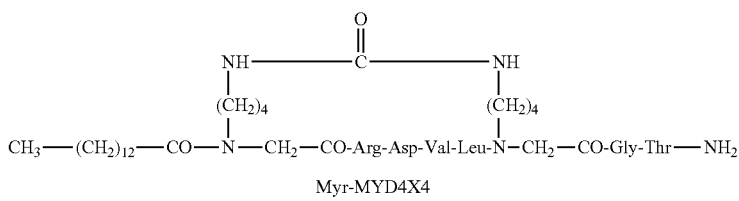

Formula VI wherein m and n are each independently an integer selected from 2, 3, 4 and 6.

Combinations of substitutions, additions and bridge modifications described with respect to specific embodiments, as well as combination of such substitutions, additions or modifications with deletion of 1-2 amino acid residues, are also within the scope of the present invention.

The peptide of present invention may be produced by any synthetic method known in the art, including but not limited to solid phase peptide synthesis.

Pharmaceutical compositions comprising at least one backbone cyclized peptide described above are provided according to another aspect of the present invention, as well as their use in treatment of diseases and disorders associated with MyD88 signaling.

Pharmaceutical compositions for use in accordance with the present invention may be formulated in conventional manner using one or more physiologically acceptable carriers comprising excipients and auxiliaries, which facilitate processing of the active compounds into preparations, which, can be used pharmaceutically. Proper formulation is dependent upon the route of administration chosen.

According to some embodiments, the pharmaceutical compositions are formulated for oral administration.

According to other embodiments, the pharmaceutical compositions are formulated for parenteral administration.

According to some embodiments, the formulation further comprises an excipient, carrier or diluent suitable for oral administration. Suitable pharmaceutically acceptable excipients for use in this invention include those known to a person ordinarily skilled in the art such as diluents, fillers, binders, disintegrants and lubricants. Diluents may include but not limited to lactose, microcrystalline cellulose, dibasic calcium phosphate, mannitol, cellulose and the like. Binders may include but not limited to starches, alginates, gums, celluloses, vinyl polymers, sugars and the like. Lubricants may include but not limited to stearates such as magnesium stearate, talc, colloidal silicon dioxide and the like.

The present invention provides, according to another aspect, a method of prevention, alleviation or treatment of a disease or disorder associated with MyD88 signaling comprising administering to a subject in need thereof, a pharmaceutically active amount of a backbone cyclic peptide analog according to the invention.

According to certain embodiments the disease or disorder associated with MyD88 signaling is an inflammatory disease or an autoimmune disease.

According to some embodiments, the autoimmune disease is selected from the group consisting of: multiple sclerosis, rheumatoid arthritis, diabetes, Sjogren's, Inflammatory Bowel Disease, Psoriasis, Pemphigus, Lupus, Grave's disease and Hashimoto's thyroiditis, Myasthenia gravis, autoimmune vasculitides, scleroderma.

According to a specific embodiment, the disease associated with MyD88 signaling is MS. According to some embodiments, the MS is selected from the group consisting of relapsing remitting MS, secondary progressive MS, primary progressive MS, and progressive relapsing MS.

According to some embodiments, the inflammatory disease or disorder is selected from the group consisting of: atherosclerosis, deficiency of the Interleukin-1 Receptor Antagonist (DIRA), sepsis, acute lung injury, and management of allo-reactive responses (such as during bone marrow or organ transplantation).

According to some embodiments, the disease or disorder associated with MyD88 signaling is associate with tissue injury, including but not limited to ischemia reperfusion (for example, in the brain, heart, intestines or kidney) and tissue graft dysfunction.

According to other embodiments, the disease or disorder associated with MyD88 signaling is lymphoma.

According to yet other embodiments, the disease or disorder associated with MyD88 signaling is lymphoma associated with a mutation in MyD88, or a solid tumor.

According to some embodiments the pharmaceutical composition is administered through a route selected from the group consisting of: orally, topically, intranasally, subcutaneously, intramuscularly, intravenously, intra-arterially, intraarticulary, intralesionally or parenterally.

The present invention provides, according to yet another aspect, a fusion protein comprising the MyD88 TIR domain sequence:

```
                                          (SEQ ID NO: 3)
DDPLGHMPERFDAFICYCPSDIQFVQEMIRQLEQTNYRLKLCVSDRDVLP

GTCVWSIASELIEKRCRRMVVVVSDDYLQSKECDFQTKFALSLSPGAHQK

RLIPIKYKAMKKEFPSILRFITVCDYTNPCTKSWFWTRLAKALSLP
``` and a carrier protein.

Any protein known in the art as suitable for use as a carrier can be used according to the present invention for the fusion proteins.

According to some embodiments, the carrier protein is SUMO3 (accession number NP_008867).

According to other embodiments, the carrier protein comprises an Fc region of an immunoglobulin.

Any method known in the art for producing and purifying fusion proteins may be used according to the present invention, including recombinant and synthetic methods.

The present invention provides, according to yet another aspect, a screening assay for identifying a compound that binds to the BB loop of MyD88 TIR domain, the method is based on binding of tagged RDVLPGT (SEQ ID NO: 1) peptide, to a fusion protein comprising the MyD88 TIR domain sequence in the presence of screened compound/s or control, and comparing the signal of the tested compound with the signal of a control, wherein significant reduction of the RDVLPGT (SEQ. ID NO: 1) peptide bound to the fusion protein indicates a compound that binds to the BB loop of MyD88 TIR domain.

According to some embodiments, the fusion protein comprises the MyD88 TIR domain having a sequence set forth in SEQ ID NO: 3, and a carrier protein.

Suitable protein molecules for use as carriers for polypeptides are known in the art and can be used for the fusion proteins of the present invention.

According to some embodiments, the fusion protein is selected from the protein SUMO3 (accession number NP_008867), and the Fc region of an immunoglobulin.

The screening assay may be performed in any format known in the art including solution and solid phase assays such as, for example ELISA, RIA and FRET.

The RDVLPGT (SEQ. ID NO: 1) peptide may be labeled with any molecule known in the art for detection, including but not limited to biotin (to be detected using Avidin), fluorescent probes and radioactive probes. In some cases, the RDVLPGT (SEQ. ID NO: 1) peptide may be used without labeling and its binding can be detected using for example mass spectroscopy methods.

According to some specific embodiments, the screening assay comprises the steps:
  (i) Producing and purifying a fusion protein comprising the MyD88 TIR domain set forth in SEQ ID NO: 3 and the protein SUMO3 (accession number NP_008867), or another appropriate fusion protein such as the Fc region of immunoglobulins;
  (ii) Coating a solid support with the fusion protein of (i);
  (iii) Adding to the coated solid support of (ii) biotinylated RDVLPGT (SEQ ID NO: 1) peptide in the presence of screened compound/s or control, and incubating for a period of time to allow binding;
  (iv) Washing unbound material and incubating with streptavidin conjugated to an enzyme such as horse radish peroxidase (HRP);
  (v) Washing unbound material, addition of a substrate and determining the signal to detect bound;
  (vi) Comparing the signal of the tested compound with the signal of a control, wherein significant reduction of the biotinylated RDVLPGT (SEQ. ID NO: 1) peptide bound to the fusion protein indicates a compound that binds to the BB loop of MyD88 TIR domain.

According to some embodiments, the screened compound/s or control of step (iii) is added 5-45 minutes prior to the biotinylated peptide.

According to some embodiments, screening is performed in solution using FRET by tagging the peptide with a fluorescent donor and adding an antibody to the SUMO3 or to its His-tag that has the fluorescent acceptor molecule.

According to some embodiments, the fusion protein of (i) is produced as a recombinant protein.

According to some embodiments, the solid support of (ii) is a 96 well plate and a library of compounds is screened for identifying a binding compound.

The assay can be used to screen chemical and biological compounds including libraries.

According to some embodiments, the screening assay is used for identifying a compounds which binds to the BB loop of MyD88 TIR domain and inhibits its signaling.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIGS. 17A and 17B. 4×4MyDI is metabolically stable in comparison to the linear MyDI peptide. 4×4MyDI vs. linear MyDI heptapeptide were incubated independently in either human plasma (18A) or human plasma supplemented with Brush Border Membrane Vesicles (BBMV, 18B). At various time points the solution was sampled and the amount of remaining compound was determined by quantitative HPLC.

DETAILED DESCRIPTION OF THE INVENTION

Figure 1A:
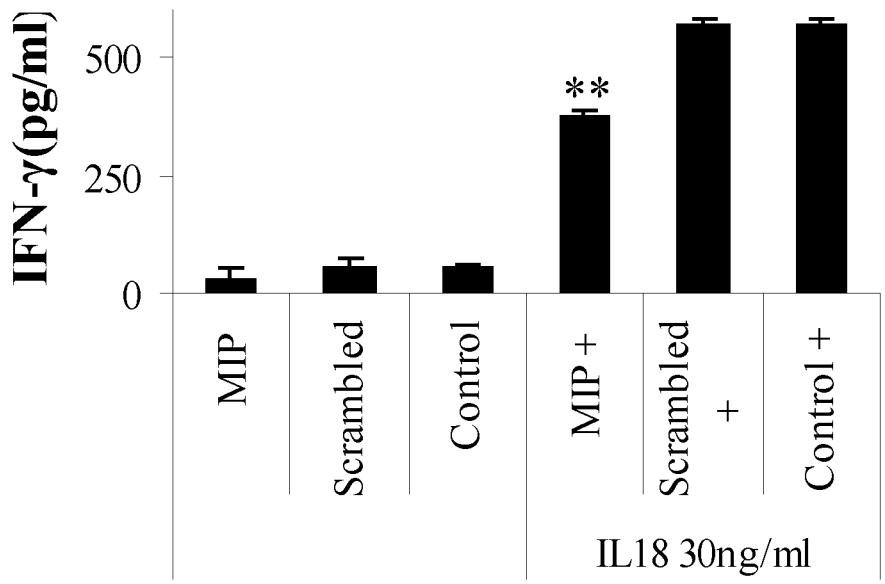
FIG. 1. MyD88 inhibitor linear peptide down-regulates IL-18-induced T-cell interferon gamma (IFN-γ) production in vitro. A: MOG35-55 specific T cells were incubated with MIP (SEQ ID NO: 1), or the scrambled version of MIP (MIPscr, PTDLVRG, SEQ ID NO: 5), or without peptide (control) for 2 h. T-cells were then plated with (right side of graph) or without (left side of graph) 30 ng/ml IL-18 for 22 h and IFN-γ production was measured by ELISA. Asterisks denote P<0.0001 compared to no inhibitor peptide or MIPscr. B: MOG35-55 specific T cells were incubated with MIP (SEQ ID NO: 1), or the scrambled version of MIP (MIPscr, SEQ ID NO: 5), or without peptide (control) for 2 h. T-cells were then plated with (right side of graph) or without (left side of graph) 30 ng/ml IL-18 for 22 h in the presence of irradiated splenocytes and MOG35-55 peptide (MEVG-WYRSPFSRVVHLYRNGK, SEQ ID NO: 4) (5 μg/ml). IFN-γ production was measured by ELISA. Asterisks denote P<0.0001 compared to no inhibitor peptide.

In the search for a MyD88 dimerization and activity inhibitor, a potent group of backbone cyclic peptides have been designed and identified as effective, stable and permeable inhibitors of the protein activity. The combination of backbone cyclization and sequence mimetics lead to cyclic peptides with improved "drug-like" properties, resembling the native peptide's conformation and enabling metabolic stability and tissue permeability which is particularly important when attempting to inhibit this intracellular adaptor protein. Applying backbone cyclization, for stabilizing the structure of a peptide in an active conformation is not obvious since activity can be lost upon substitution of original residues with N-alkylated amino acid residues and the exact position and nature of the connecting building units and bridge should be determined.

In this effort, a library of metabolically stable cyclic peptides was generated using backbone cyclization of the MyDI 7 amino acid linear peptide (RDVLPGT SEQ ID NO: 1) that corresponds to the "BB loop" of the MyD88 TIR domain. The library was screened using a functional assay and a lead compound has been identified demonstrating protease resistance and enhanced intracellular penetration, pharmacological properties that will enable in vivo use by oral delivery upon further development.

The fact that lead compound is designed to be deliverable by the oral route, is of great improvement in treating MS as most of the disease modifying agents in use (for example Copaxone and Betaferon), are administered by injection.

In addition, the lead compound interferes with a pathway (MyD88 signaling) not previously targeted in MS, and it therefore may complement existing solutions.

MyD88 is a key signaling protein downstream of Toll like receptors and receptors for pro-inflammatory cytokines such as the IL-1 family (e.g. IL-1, IL-18, IL-33). The absence of MyD88, or inhibition of MyD88, lowers inflammation and leads to disease resistance in the animal model of MS (EAE). MyD88-signaling is also implicated in other autoimmune diseases, in hyper-inflammatory conditions, in lymphoma, and cancer, presenting additional significant medical indications that can be addressed with a stable, pharmacologically-active drug lead.

Cyclic peptides usually show higher metabolic stability and improved epithelial permeability compared to the linear peptide, possibly due to reduced degrees of freedom of the peptide and stabilization in a favorable conformation for higher permeability but cyclization per-se may not be sufficient enough to improve the intestinal permeability of hydrophilic peptides, especially those of the MyD88 BB loop that have positively charged residues (Arg), and a free amino terminus.

Without wishing to be bound to any theory of mechanism of action, it is proposed that inhibition of MyD88 should influence the cytokine profile of autoimmune T cells by blocking costimulatory molecule expression by antigen presenting cells (APCs), and by inhibiting the T cell response to IL-1/IL-18/IL-33. It is now shown for the first time that inhibition of MyD88 lowers murine and human T cell IFNγ production in vitro in response to IL-12/IL-18 stimulation. Furthermore, shRNA silencing of MyD88 in human APCs led to decreased IFNγ production by responding T cells. Finally, it is the first time to demonstrate that systemic MyD88 antagonism using the linear BB loop 7 amino acid peptide (RDVLPGT, SEQ. ID NO: 1) significantly reduced the clinical manifestations of EAE in mice. Thus, MyD88 appears to be a key factor in determining the cytokine phenotype of T cells involved in autoimmune inflammation, and represents a potential target for therapeutic intervention.

As presented in the experimental section and figures, the activity of representative compounds of the present invention has been demonstrated in multiple assays:

i. Inhibition of human macrophage inflammatory cytokine production upon stimulation with a TLR2 ligand (TLR2 signaling is dependent upon MyD88).

ii. Specificity of inhibition by activated cells with either IL-1b (MyD88 dependent), or with TNFα (MyD88 independent), demonstrating that the 4x4MyDI is a specific inhibitor.

iii. Inhibition of T cells activated with IL-18 demonstrating the broad effect of a MyD88 inhibitor. Since IL-18 is an IL-1 cytokine family member, its receptor is also dependent upon MyD88 for signaling.

iv. Physical binding of 4x4MyDI to the MyD88 parent molecule and interfering with its dimerization.

v. The therapeutic efficacy of the 4x4MyDI in the animal EAE model of multiple sclerosis.

vi. The permeability properties of 4x4MyDI in two different cellular models.

In the aim to identify an inhibitor of MyD88, a competition screening assay has been developed. In this assay, the MyD88 TIR domain was expressed as a recombinant fusion protein with a carrier protein and attached to an ELISA plate. Using this assay as a screening tool, it was demonstrated that the 4x4myd backbone cyclic peptide of the present invention competitively inhibits binding of a biotinylated version of the linear BB loop peptide, to the MyD88 polypeptide on the coated plate. This assay establishes that the backbone cyclic 4x4mydI binds to the same region as the linear BB loop peptide, i.e. the BB loop interface itself (which is responsible for MyD88 dimerization).

Cyclic Peptides and Backbone Cyclization

Cyclization of peptides has been shown to be a useful approach in developing diagnostically and therapeutically useful peptidic and peptidomimetic agents. Cyclization of peptides reduces the conformational freedom of these flexible, linear molecules, and often results in higher receptor binding affinities by reducing unfavorable entropic effects. Because of the more constrained structural framework, these agents are more selective in their affinity to specific receptor cavities. By the same reasoning, structurally constrained cyclic peptides confer greater stability against the action of proteolytic enzymes (Humphrey, et al., 1997, Chem. Rev., 2243-2266).

Methods for cyclization can be classified into cyclization by the formation of the amide bond between the N-terminal and the C-terminal amino acid residues, and cyclizations involving the side chains of individual amino acids. The latter method includes the formation of disulfide bridges between two ω-thio amino acid residues (cysteine, homo-cysteine), the formation of lactam bridges between glutamic/ aspartic acid and lysine residues, the formation of lactone or thiolactone bridges between amino acid residues containing carboxyl, hydroxyl or mercapto functional groups, the formation of thioether or ether bridges between the amino acids containing hydroxyl or mercapto functional groups and other special methods. Lambert, et al., reviewed variety of peptide cyclization methodologies (J. Chem. Soc. Perkin Trans., 2001, 1:471-484).

Backbone cyclization is a general method by which conformational constraint is imposed on peptides. In backbone cyclization, atoms in the peptide backbone (N and/or C) are interconnected covalently to form a ring. Backbone cyclized analogs are peptide analogs cyclized via bridging groups attached to the alpha nitrogens or alpha carbonyl of amino acids. In general, the procedures utilized to construct such peptide analogs from their building units rely on the known principles of peptide synthesis; most conveniently, the procedures can be performed according to the known principles of solid phase peptide synthesis. During solid phase synthesis of a backbone cyclized peptide the protected building unit is coupled to the N-terminus of the peptide chain or to the peptide resin in a similar procedure to the coupling of other amino acids. After completion of the peptide assembly, the protective group is removed from the building unit's functional group and the cyclization is accomplished by coupling the building unit's functional group and a second functional group selected from a second building unit, a side chain of an amino acid residue of the peptide sequence, and an N-terminal amino acid residue.

As used herein the term "backbone cyclic peptide" or "backbone cyclic analog" refers to a sequence of amino acid residues wherein at least one nitrogen or carbon of the peptide backbone is joined to a moiety selected from another such nitrogen or carbon, to a side chain or to one of the termini of the peptide. According to specific embodiment of the present invention the peptide sequence is of 5 to 15 amino acids that incorporates at least one building unit, said building unit containing one nitrogen atom of the peptide backbone connected to a bridging group comprising an amide, thioether, thioester, disulfide, urea, carbamate, or sulfonamide, wherein at least one building unit is connected via said bridging group to form a cyclic structure with a moiety selected from the group consisting of a second building unit, the side chain of an amino acid residue of the sequence or a terminal amino acid residue. Furthermore, one or more of the peptide bonds of the sequence may be reduced or substituted by a non-peptidic linkage.

A "building unit" (BU) indicates a $N^{\alpha}$-ω-functionalized or an $C^{\alpha}$-ω-functionalized derivative of amino acids. Use of such building units permits different length and type of linkers and different types of moieties to be attached to the scaffold. This enables flexible design and easiness of production using conventional and modified solid-phase peptide synthesis methods known in the art.

In general, the procedures utilized to construct backbone cyclic molecules and their building units rely on the known principles of peptide synthesis and peptidomimetic synthesis; most conveniently, the procedures can be performed according to the known principles of solid phase peptide synthesis. Some of the methods used for producing $N^{\alpha}$ω building units and for their incorporation into peptidic chain are disclosed in U.S. Pat. Nos. 5,811,392; 5,874,529; 5,883,293; 6,051,554; 6,117,974; 6,265,375, 6,355613, 6,407059, 6,512092 and international applications WO 95/33765; WO 97/09344; WO 98/04583; WO 99/31121; WO 99/65508; WO 00/02898; WO 00/65467 and WO 02/062819.

As used herein "peptide" indicates a sequence of amino acids linked by peptide bonds. Functional derivatives of the peptides of the invention covers derivatives which may be prepared from the functional groups which occur as side chains on the residues or the N- or C-terminal groups, by means known in the art, and are included in the invention. These derivatives may, for example, include aliphatic esters of the carboxyl groups, amides of the carboxyl groups produced by reaction with ammonia or with primary or secondary amines, N-acyl derivatives of free amino groups of the amino acid residues formed by reaction with acyl moieties (e.g., alkanoyl or carbocyclic aroyl groups) or O-acyl derivatives of free hydroxyl groups (for example those of seryl or threonyl residues) formed by reaction with acyl moieties. Salts of the peptides of the invention contemplated by the invention are organic and inorganic salts.

The compounds herein disclosed may have asymmetric centers. All chiral, diastereomeric, and racemic forms are included in the present invention. Many geometric isomers of double bonds and the like can also be present in the compounds disclosed herein, and all such stable isomers are contemplated in the present invention.

"Derivatives" of the peptides of the invention as used herein covers derivatives which may be prepared from the functional groups which occur as side chains on the residues or the N- or C-terminal groups, by means known in the art, and are included in the invention as long as they remain pharmaceutically acceptable, i.e., they do not destroy the activity of the peptide, do not confer toxic properties on compositions containing it, and do not adversely affect the immunogenic properties thereof.

These derivatives may include, for example, aliphatic esters of the carboxyl groups, amides of the carboxyl groups produced by reaction with ammonia or with primary or secondary amines, N-acyl derivatives of free amino groups of the amino acid residues formed by reaction with acyl moieties (e.g., alkanoyl or carbocyclic aroyl groups), or O-acyl derivatives of free hydroxyl group (e.g., that of seryl or threonyl residues) formed by reaction with acyl moieties.

The term "analog" further indicates a molecule which has the amino acid sequence according to the invention except for one or more amino acid changes. Analogs according to the present invention may comprise also peptidomimetics. "Peptidomimetic" means that a peptide according to the invention is modified in such a way that it includes at least one non-coded residue or non-peptidic bond. Such modifications include, e.g., alkylation and more specific methylation of one or more residues, insertion of or replacement of natural amino acid by non-natural amino acids, replacement of an amide bond with another covalent bond. A peptidomimetic according to the present invention may optionally comprise at least one bond which is an amide-replacement bond such as urea bond, carbamate bond, sulfonamide bond, hydrazine bond, or any other covalent bond. The design of appropriate "analogs" may be computer assisted. Analogs are included in the invention as long as they remain pharmaceutically acceptable.

Reference to a particular peptide or "analog" includes the naturally occurring peptide sequence or a peptide that has the substantially the same activity as the naturally occurring sequence. "Peptides" of the invention also include modified peptides (with amino acid substitutions, both conservative and non-conservative as described below) that have the same or improved activity as a wild-type or unmodified peptide. "Salts" of the peptides of the invention contemplated by the invention are physiologically and pharmaceutically acceptable organic and inorganic salts.

The term "amino acid" refers to compounds, which have an amino group and a carboxylic acid group, preferably in a 1,2- 1,3-, or 1,4-substitution pattern on a carbon backbone. α-Amino acids are most preferred, and include the 20 natural amino acids (which are L-amino acids except for glycine) which are found in proteins, the corresponding D-amino acids, the corresponding N-methyl amino acids, side chain modified amino acids, the biosynthetically available amino acids which are not found in proteins (e.g., 4-hydroxy-proline, 5-hydroxy-lysine, citrulline, ornithine, canavanine, djenkolic acid, β-cyanolanine), and synthetically derived α-amino acids, such as amino-isobutyric acid, norleucine, norvaline, homocysteine and homoserine. β-Alanine and γ-amino butyric acid are examples of 1,3 and 1,4-amino acids, respectively, and many others are well known to the art.

Some of the amino acids used in this invention are those which are available commercially or are available by routine synthetic methods. Certain residues may require special methods for incorporation into the peptide, and either sequential, divergent or convergent synthetic approaches to the peptide sequence are useful in this invention. Natural coded amino acids and their derivatives are represented by three-letter codes according to IUPAC conventions. When there is no indication, the L isomer was used. The D isomers are indicated by "D" or "(D)" before the residue abbreviation.

Conservative substitution of amino acids as known to those skilled in the art are within the scope of the present invention. Conservative amino acid substitutions includes replacement of one amino acid with another having the same type of functional group or side chain e.g. aliphatic, aromatic, positively charged, negatively charged. One of skill will recognize that individual substitutions, deletions or additions to peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
 1) Alanine (A), Serine (S), Threonine (T);
 2) Aspartic acid (D), Glutamic acid (E);
 3) Asparagine (N), Glutamine (Q);
 4) Arginine (R), Lysine (K), Histidine (H);
 5) Isoleucine (I), Leucine (L), Methionine (M), Valine (V); and
 6) Phenylalanine (F), Tyrosine (Y), Tryptophan (W).

The backbone cyclic peptides of present invention may be produced by any method known in the art enabling the creation of such molecules. Synthetic methods include exclusive solid phase synthesis, partial solid phase synthesis, fragment condensation, or classical solution synthesis. Solid phase peptide synthesis procedures are well known to one skilled in the art and. In some embodiments, synthetic peptides are purified by preparative high performance liquid chromatography and the peptide sequence is confirmed via amino acid sequencing by methods known to one skilled in the art.

"Permeability" refers to the ability of an agent or substance to penetrate, pervade, or diffuse through a barrier, membrane, or a skin layer. A "cell permeability moiety", a "permeability enhancing moiety" or a "cell-penetration moiety" refers to any molecule known in the art which is able to facilitate or enhance penetration of molecules through membranes. Non-limitative examples include: hydrophobic moieties such as lipids, fatty acids, steroids and bulky aromatic or aliphatic compounds; hydrophilic moieties such as Arginine residues or guanidino-containing moieties; moieties which may have cell-membrane receptors or carriers, such as steroids, vitamins and sugars, natural and non-natural amino acids and transporter peptides.

The hydrophobic moiety according to the invention may comprise a lipid moiety or an amino acid moiety. According to a specific embodiment the hydrophobic moiety is selected from the group consisting of: phospholipids, steroids, sphingosines, ceramides, octyl-glycine, 2-cyclohexylalanine, benzolylphenylalanine, propionoyl ($C_3$); butanoyl ($C_4$); pentanoyl ($C_5$); caproyl ($C_6$); heptanoyl ($C_7$); capryloyl ($C_8$); nonanoyl ($C_9$); capryl ($C_{10}$); undecanoyl ($C_{11}$); lauroyl ($C_{12}$); tridecanoyl ($C_{13}$); myristoyl ($C_{14}$); pentadecanoyl ($C_{15}$); palmitoyl ($C_{16}$); phtanoyl (($CH_3$)$_4$); heptadecanoyl ($C_{17}$); stearoyl ($C_{18}$); nonadecanoyl ($C_{19}$); arachidoyl ($C_{20}$); heniecosanoyl ($C_{21}$); behenoyl ($C_{22}$); trucisanoyl ($C_{23}$); and lignoceroyl ($C_{24}$); wherein said hydrophobic moiety is attached to said chimeric polypeptide with amide bonds, sulfhydryls, amines, alcohols, phenolic groups, or carbon-carbon bonds.

Other examples for lipidic moieties which may be used according to the present invention: Lipofectamine, Transfectace, Transfectam, Cytofectin, DMRIE, DLRIE, GAP-DLRIE, DOTAP, DOPE, DMEAP, DODMP, DOPC, DDAB, DOSPA, EDLPC, EDMPC, DPH, TMADPH, CTAB, lysyl-PE, DC-Cho, -alanyl cholesterol; DCGS, DPPES, DCPE, DMAP, DMPE, DOGS, DOHME, DPEPC, Pluronic, Tween, BRIJ, plasmalogen, phosphatidylethanolamine, phosphatidylcholine, glycerol-3-ethylphosphatidylcholine, dimethyl ammonium propane, trimethyl ammonium propane, diethylammonium propane, triethylammonium propane, dimethyldioctadecylammonium bromide, a sphingolipid, sphingomyelin, a lysolipid, a glycolipid, a sulfatide, a glycosphingolipid, cholesterol, cholesterol ester, cholesterol salt, oil, N-succinyldioleoylphosphatidylethanolamine, 1,2-dioleoyl-sn-glycerol, 1,3-dipalmitoyl-2-succinylglycerol, 1,2-dipalmitoyl-sn-3-succinylglycerol, 1-hexadecyl-2-palmitoylglycerophosphatidylethanolamine, palmitoylhomocystiene, N,N'-Bis (dodecyaminocarbonylmethylene)-N,N'-bis((-N,N,N-trimethylammoniumethyl-aminocarbonylmethylene)ethylenediamine tetraiodide; N,N''-Bis(hexadecylaminocarbonylmethylene)-N,N',N''-tris((-N,N,N-trimethylammonium-ethylaminocarbonylmethylenediethylenetri amine hexaiodide; N,N'-Bis(dodecylaminocarbonylmethylene)-N,N'''-bis((-N, N,N-trimethylammonium ethylaminocarbonylmethylene) cyclohexylene-1,4-diamine tetraiodide; 1,7,7-tetra-((-N,N, N,N-tetramethylammoniumethylamino-carbonylmethylene)-3-hexadecylaminocarbonyl-methylene-1,3,7-triaazaheptane heptaiodide; N,N,N',N'-tetra((-N,N,N-trimethylammonium-ethylaminocarbonylmethylene)-N'— (1,2-dioleoylglycero-3-phosphoethanolamino carbonylmethylene)diethylenetriam ihe tetraiodide; dioleoylphosphatidylethanolamine, a fatty acid, a lysolipid, phosphatidylcholine, phosphatidylethanolamine, phosphatidylserine, phosphatidylglycerol, phosphatidylinositol, a sphingolipid, a glycolipid, a glucolipid, a sulfatide, a glycosphingolipid, phosphatidic acid, palmitic acid, stearic acid, arachidonic acid, oleic acid, a lipid bearing a polymer, a lipid bearing a sulfonated saccharide, cholesterol, tocopherol hemisuccinate, a lipid with an ether-linked fatty acid, a lipid with an ester-linked fatty acid, a polymerized lipid, diacetyl phosphate, stearylamine, cardiolipin, a phospholipid with a fatty acid of 6-8 carbons in length, a phospholipid with asymmetric acyl chains, 6-(5-cholesten-3b-yloxy)-1-thio-b-D-galactopyranoside, digalactosyldiglyceride, 6-(5-cholesten-3b-yloxy)hexyl-6-amino-6-deoxy-1-thio-b-D-galactopyranoside, 6-(5-cholesten-3b-yloxy)hexyl-6-amino-6-deoxyl-1-thio-a-D-mannopyranoside, 12-(((7'-diethylamino-coumarin-3-yl)carbonyl)methylamino)-octadecanoic acid; N-[12-(((7'-diethylaminocoumarin-3-yl)carbonyl)methylamino) octadecanoyl]-2-aminopalmitic acid; cholesteryl)4'-trimethyl-ammonio)butanoate; N-succinyldioleoyl-phosphatidylethanolamine; 1,2-dioleoyl-sn-glycerol; 1,2-dipalmitoyl-sn-3-succinyl-glycerol; 1,3-dipalmitoyl-2-succinylglycerol, 1-hexadecyl-2-palmitoylglycerophosphoethanolamine, and palmitoylhomocysteine.

Pharmacology

The compounds of the present invention can be formulated into various pharmaceutical forms for purposes of administration. Pharmaceutical composition of interest may comprise at least one additive selected from a disintegrating agent, binder, flavoring agent, preservative, colorant and a mixture thereof, as detailed for example in "Handbook of Pharmaceutical Excipients"; Ed. A. H. Kibbe, 3rd Ed., American Pharmaceutical Association, USA.

For example, a compound of the invention, or its salt form or a stereochemically isomeric form, can be combined with a pharmaceutically acceptable carrier. Such a carrier can depend on the route of administration, such as oral, rectal, percutaneous or parenteral injection.

A "carrier" as used herein refers to a non-toxic solid, semisolid or liquid filler, diluent, vehicle, excipient, solubilizing agent, encapsulating material or formulation auxiliary of any conventional type, and encompasses all of the components of the composition other than the active pharmaceutical ingredient. The carrier may contain additional agents such as wetting or emulsifying agents, or pH buffering agents. Other materials such as anti-oxidants, humectants, viscosity stabilizers, and similar agents may be added as necessary.

For example, in preparing the compositions in oral dosage form, media such as water, glycols, oils, alcohols can be used in liquid preparations such as suspensions, syrups, elixirs, and solutions. Alternatively, solid carriers such as starches, sugars, kaolin, lubricants, binders, disintegrating agents can be used, for example, in powders, pills, capsules or tablets.

The pharmaceutically acceptable excipient(s) useful in the composition of the present invention are selected from but not limited to a group of excipients generally known to persons skilled in the art e.g. diluents such as lactose (Pharmatose DCL 21), starch, mannitol, sorbitol, dextrose, microcrystalline cellulose, dibasic calcium phosphate, sucrose-based diluents, confectioner's sugar, monobasic calcium sulfate monohydrate, calcium sulfate dihydrate, calcium lactate trihydrate, dextrates, inositol, hydrolyzed cereal solids, amylose, powdered cellulose, calcium carbonate, glycine, and bentonite; disintegrants; binders; fillers; bulking agent; organic acid(s); colorants; stabilizers; preservatives; lubricants; glidants/antiadherants; chelating agents; vehicles; bulking agents; stabilizers; preservatives; hydrophilic polymers; solubility enhancing agents such as glycerin, various grades of polyethylene oxides, transcutol and glycofiirol; tonicity adjusting agents; pH adjusting agents; antioxidants; osmotic agents; chelating agents; viscosifying agents; wetting agents; emulsifying agents; acids; sugar alcohol; reducing sugars; non-reducing sugars and the like, used either alone or in combination thereof.

The disintegrants useful in the present invention include but not limited to starch or its derivatives, partially pregelatinized maize starch (Starch 1500®), croscarmellose sodium, sodium starch glycollate, clays, celluloses, alginates, pregelatinized corn starch, crospovidone, gums and the like used either alone or in combination thereof. The lubricants useful in the present invention include but not limited to talc, magnesium stearate, calcium stearate, sodium stearate, stearic acid, hydrogenated vegetable oil, glyceryl behenate, glyceryl behapate, waxes, Stearowet, boric acid, sodium benzoate, sodium acetate, sodium chloride, DL-leucine, polyethylene glycols, sodium oleate, sodium lauryl sulfate, magnesium lauryl sulfate and the like used either alone or in combination thereof. The antiadherents or glidants useful in the present invention are selected from but not limited to a group comprising talc, corn starch, DL-leucine, sodium lauryl sulfate, and magnesium, calcium and sodium stearates, and the like or mixtures thereof. In another embodiment of the present invention, the compositions may additionally comprise an antimicrobial preservative such as benzyl alcohol. In an embodiment of the present invention, the composition may additionally comprise a conventionally known antioxidant such as ascorbyl palmitate, butylhydroxyanisole, butylhydroxytoluene, propyl gallate and/or tocopherol. In another embodiment, the dosage form of the present invention additionally comprises at least one wetting agent(s) such as a surfactant selected from a group comprising anionic surfactants, cationic surfactants, non-ionic surfactants, zwitterionic surfactants, or mixtures thereof. The wetting agents are selected from but not limited to a group comprising oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, sodium lauryl sulfate and the like, or mixtures thereof. In yet another embodiment, the dosage form of the present invention additionally comprises at least one complexing agent such as cyclodextrin selected from a group comprising but not limited to alpha-cyclodextrin, beta-cyclodextrin, betahydroxy-cyclodextrin, gamma-cyclodextrin, and hydroxypropyl beta-cyclodextrin, or the like. In yet another embodiment, the dosage form of the present invention additionally comprises of lipid(s) selected from but not limited to glyceryl behenate such as Compritol® ATO888, Compritol® ATO 5, and the like; hydrogenated vegetable oil such as hydrogenated castor oil e.g. Lubritab®; glyceryl palmitostearate such as Precirol® ATO 5 and the like, or mixtures thereof used either alone or in combination thereof. It will be appreciated that any given excipient may serve more than one function in the compositions according to the present invention.

For parenteral compositions, the carrier can comprise sterile water. Other ingredients may be included to aid in solubility. Injectable solutions can be prepared where the carrier includes a saline solution, glucose solution or mixture of both.

Injectable suspensions can also be prepared. In addition, solid preparations that are converted to liquid form shortly before use can be made. For percutaneous administration, the carrier can include a penetration enhancing agent or a wetting agent.

It can be advantageous to formulate the compositions of the invention in dosage unit form for ease of administration and uniformity of dosage. "Dosage unit form" refers to physically discrete units suitable as unitary dosages, each unit containing a pre-determined quantity of active ingredient calculated to produce the desired therapeutic effect in association with the chosen carrier.

Apart from other considerations, the fact that the novel active ingredients of the invention are peptides, peptide analogs or peptidomimetics, dictates that the formulation be suitable for delivery of these types of compounds. Although in general peptides are less suitable for oral administration due to susceptibility to digestion by gastric acids or intestinal enzymes. According to the present invention, novel methods of backbone cyclization are being used, in order to synthesize metabolically stable and oral bioavailable peptidomimetic analogs. The preferred route of administration of peptides of the invention is oral administration.

Other routes of administration are intra-articular, intravenous, intramuscular, subcutaneous, intradermal, or intrathecal.

Pharmaceutical compositions of the present invention may be manufactured by processes well known in the art, e.g., by means of conventional mixing, dissolving, granulating, grinding, pulverizing, dragee-making, levigating, emulsifying, encapsulating, entrapping or lyophilizing processes.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

For injection, the compounds of the invention may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants for example polyethylene glycol are generally known in the art.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

For buccal administration, the compositions may take the form of tablets or lozenges formulated in conventional manner.

For administration by inhalation, the variants for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the peptide and a suitable powder base such as lactose or starch.

Pharmaceutical compositions for parenteral administration include aqueous solutions of the active ingredients in water-soluble form. Additionally, suspensions of the active compounds may be prepared as appropriate oily injection suspensions. Suitable natural or synthetic carriers are well known in the art (Pillai et al., 2001, Curr. Opin. Chem. Biol. 5, 447). Optionally, the suspension may also contain suitable stabilizers or agents, which increase the solubility of the compounds, to allow for the preparation of highly concentrated solutions. Alternatively, the active ingredient may be in powder form for reconstitution with a suitable vehicle, e.g., sterile, pyrogen-free water, before use.

The compounds of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of a compound effective to prevent, alleviate or ameliorate symptoms of a disease of the subject being treated. Determination of a therapeutically effective amount is well within the capability of those skilled in the art.

Toxicity and therapeutic efficacy of the peptides described herein can be determined by standard pharmaceutical procedures in cell cultures or experimental animals, e.g., by determining the IC50 (the concentration which provides 50% inhibition) and the LD50 (lethal dose causing death in 50% of the tested animals) for a subject compound. The data obtained from these cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition (e.g. Fingl, et al., 1975, in "The Pharmacological Basis of Therapeutics", Ch. 1 p. 1).

The precise dosage and frequency of administration depends on the particular compound of the invention being used, as well as the particular condition being treated, the severity of the condition, the age, weight, and general physical condition of the subject being treated, as well as other medication being taken by the subject, as is well known to those skilled in the art. It is also known that the effective daily amount can be lowered or increased depending on the response of the subject or the evaluation of the prescribing physician. Thus, the ranges mentioned above are only guidelines and are not intended to limit the scope of the use of the invention.

The combination of a compound of the invention with another agent used for treatment of MS can be used. Such combination can be used simultaneously, sequentially or separately. Such agents may include, for example, glucocorticoids, immunomodulatory drugs such as interferon beta, glatiramer acetate, fingolimod and mitoxanthrone.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

General Procedures

Chemistry General

All starting materials were purchased from commercial sources and were used without further purification. Nuclear magnetic resonance (NMR) spectra during synthesis were recorded on a Bruker AMX 300, Bruker 400 or Bruker 500 MHz spectrometer. Chemical shifts are reported downfield, relative to internal solvent peaks. Coupling constants J are reported in Hz. High Resolution Mass spectrometry (HRMS) spectra were recorded on nanospray ionization LTQ orbitrap. Matrix assisted laser desorption ionization (MALDI)-time of flight (TOF) (MALDI-TOF) Mass spectra were recorded on a PerSeptive Biosystems MALDI-TOF MS, using α-cyano-4-hydroxycinnamic acid as matrix. Thin layer chromatography (TLC) was performed on Merck aluminum sheets silica gel 60 F254. Column chromatography was performed on Merck silica gel 60 (230-400 mesh).

Peptides purity was determined by analytical HPLC, peptides below 95% purity were excluded from further examination (see supporting information). Analytical HPLC was performed on Vydac analytical columns (C18, 5μ 4.6 mm×250 mm (218TP54)) using Merck-Hitachi system: Model LaChrom with a L-7100 pump, L-7200 autosampler, L-7400 UV/Vis detector and a D-7000 interface. Products were assayed at 215 and 220 nm. The mobile phase consisted of a gradient system, with solvent A corresponding to TDW with 0.1% TFA and solvent B corresponding to acetonitrile (ACN) with 0.1% TFA. The mobile phase started with 95% A from 0 to 5 min followed by a linear gradient from 5% B to 95% B from 5 to 55 min. The gradient remained at 95% B for an additional 5 min and then was reduced to 95% A and 5% B from 60 to 65 min. The gradient remained at 95% A for additional 5 min to achieve column equilibration. The flow rate of the mobile phase was 1 mL/min. Peptide purification was performed by reversed phase semi-preparative HPLC on a Merck-Hitachi 665A model equipped with a preparative pump (30 ml/min) and a high flow UV/Vis detector using semipreparative Vydac column (C18, 5μ, 10×250 (208TP510)) flow rate of the mobile phase was 4.5 mL/min. All semi preparative HPLC runs were carried out using a gradient system similar to the one used in for the analytical HPLC.

Analytical RP-HPLC were recorded at 220 nm at a flow of 1 ml/min on Merck-Hitachi system (LaChrom with a L-7100 pump, L-7200 autosampler, L-7400 UV/Vis detector and a D-7000 interface) on Phenomenex RP-18 column (C18, 5i, 4.6×75 mm (Luna)). Using the same solvent system previously described, the mobile phase started with 95% A from 0 to 5 min followed by a linear gradient from 5% B to 95% B from 5 to 17 min. The gradient remained at 95% B for an additional 4 min and then was reduced to 95% A from 21 to 25 min. The gradient remained at 95% A for additional 5 min to achieve column equilibration. Semi-preparative HPLC were recorded at 220 nm on Phenomenex RP-18 column (C18, 10μ 250×10 mm, 110 Å (Gemini)). Using the same solvent system previously described, the mobile phase started with 95% A from 0 to 5 min followed by a linear gradient from 5% B to 35% B from 5 to 30 min, then to 95% B in 15 min, the gradient remained at 95% B for an additional 5 min and then was reduced to 95% A in 10 min. The gradient remained at 95% A for additional 5 min to achieve column equilibration.

Assessment of Intestinal Absorption Properties

Transport studies are performed through the CaCO-2 monolayer (passage range of 52-60) seeded at density of $25×10^5$ cells/cm$^2$ on untreated culture inserts of polycarbonate membrane with 0.4 μm pores and surface of 1.1 cm$^2$. The culture inserets containing Caco-2 monolayers were place in 24 transwell plates 12 mm, Costar™. The cells were monitored for their transepithelial electrical resistance (TEER) measurements to assure TEER between 300 and 500 $Ω*cm^2$. Specific markers for paracellular and transcellular permeability pathways are used to ensure the validity of the permeability results of the tested compounds. HBSS supplemented with 10 mM MES and adjusted to pH 6.5 will be used as transport medium in the donor compartment and pH 7.4 in the acceptor compartment. The donor solution contains the test compound. The effective permeability coefficient is calculated from concentration-time profiles of each of the tested compounds in the acceptor chamber.

In Vivo Studies

Effective peptides are examined for treatment of mice with EAE (the animal model of MS) applying several disease models. One model is described in Owens T. and Sriram S. Neurologic Clinics (1995) 13(1):51-73. In this model, C57B1 mice are immunized with the MOG protein in adjuvant and the onset of paralysis which appears 10-14 days following the induction, is evaluated daily. Two groups of animals are treated with two doses of the peptide administered orally by cannula on a daily basis, from the day of EAE-induction. One month after the disease onset, the animals are sacrificed and their brains and spinal cords are processed for histopathological analysis (performed by a blinded for the treatment arm, neuropathologist). This includes the evaluation of the number of inflammatory infiltrates and the number of cells per infiltrate, the degree of demyelination and of axonal damage. Another EAE model for MS which can be used for the compounds of the present invention and for identifying additional Myd88 inhibitors is described in Prinz et al 2006, J Clin Investigation, 116, 2 456-464, and Cohen et al 2010, J Immunol 184(1):212-21). In this model, C57B1 mice are immunized with MOG35-55 peptide (MEVGWYRSPFSRVVHLYRNGK, SEQ ID NO: 4) emulsified in complete Freund's adjuvant (CFA) and pertussis toxin is administered systemically at the time of immunization and 48 h later. Mice are treated with the Myd88 inhibitor systemically and the mice are followed for development of ascending paralysis which typically begins on day 8-10 following immunization.

EXAMPLES

Figure 1B:
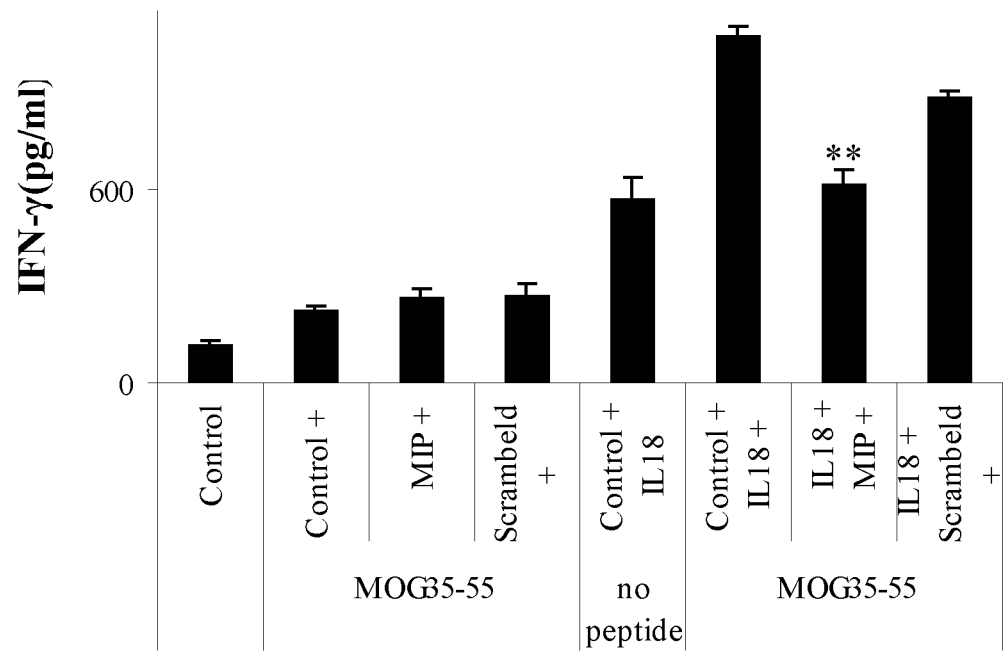

Example 1. MyD88 Inhibitor Linear Peptide Reduces IFN-γ Secreted by IL-18 Activation of Anti-MOG35-55 T-Cells To investigate the ability of the MyD88 inhibitor linear peptide (termed either MIP or MyDI) to inhibit MyD88 activity in T-cells in vitro, the secretion of IFN-γ by MOG-specific T cells in response to IL-18 stimulation was tested. The signaling of IL-18 trough the IL-18 receptor is MyD88 dependent. Cells were treated with MIP (SEQ ID NO: 1, 20 mM peptide for 1 h at 37° C.;), or with a scrambled version of the peptide (PTDLVRG, SEQ ID NO: 5), as a control. Cells were then stimulated with IL-18, and IFN-γ levels in the supernatants were analyzed after 24 h. As demonstrated in FIG. 1A, MIP treatment significantly reduced the IL-18-stimulated IFNγ level whereas the scrambled version of MIP had no effect. Next, the effect of MIP on the cytokine response of MOG-specific T cells responding to antigen stimulation (APC presenting MOG35-55 peptide) in the presence of IL-18 stimulation was tested. As shown in FIG. 1B IL-18 treatment increased the IFN-γ response of antigen-specific T cells from 300 to 900 pg/ml and MIP treatment reduced the level of IFN-γ by 30-35%.

Example 2. MIP Treatment Significantly Inhibits EAE

Figure 2:
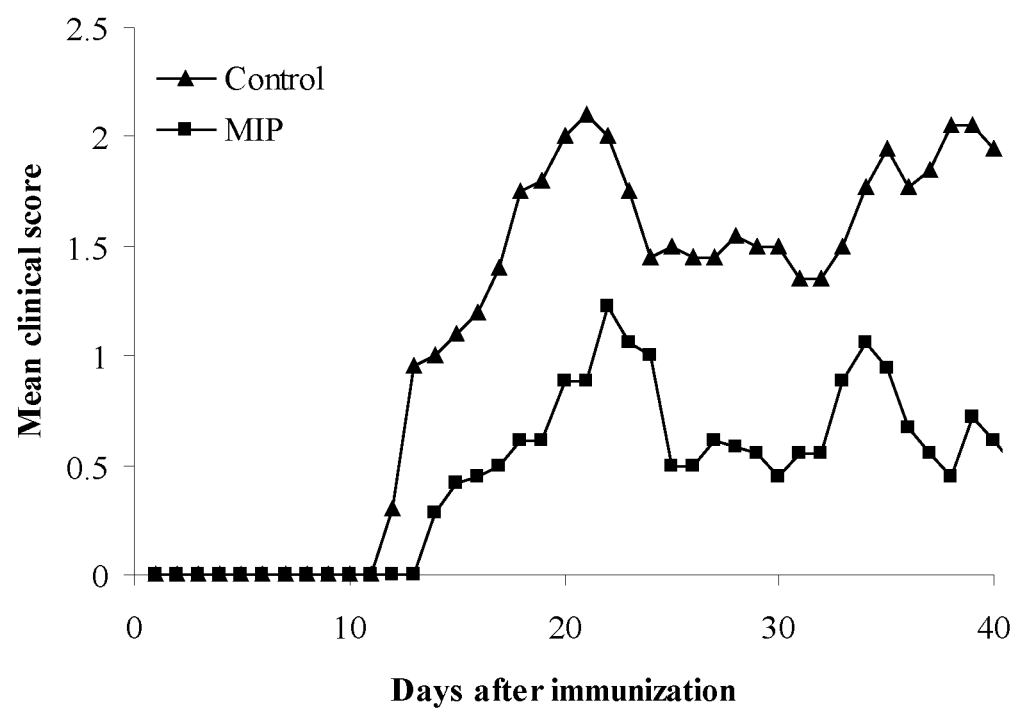
FIG. 2. MIP treatment reduces severity of EAE. Mice were immunized with MOG35-55/CFA with PTX administration at day 0 and at 48 h. Groups of mice were treated with MIP (SEQ ID NO: 1, squares) or PBS (triangles) and mean clinical score was calculated.

The effect of MIP administration on the clinical outcome of MOG35-55/CFA induced EAE was tested. Mice were treated with 2 mg/Kg of MIP (SEQ ID NO: 1) vs. MIP scrambled (SEQ ID NO: 5), or PBS (200 µl) i.p. three times a week beginning on the day of immunization with MOG35-55/CFA. The two control groups, MIP scrambled (SEQ ID NO: 5), and PBS treated mice, behaved similarly and were joined for comparison to the active treatment group. As shown in FIG. 2, the MIP treated mice were protected from EAE. The disease incidence, cumulative mean clinical score, and mean score on individual days were significantly lower in MIP-treated mice. Differences in disease incidence, cumulative disease score, and clinical score on individual days are presented in Table 1 (*p<0.05):

TABLE 1

| Treatment | Incidence | Cumulative mean clinical score | Days after injection* |
|---|---|---|---|
| MIP | 4 of 9 | 18.6 ± 9* | 20, 25, 27-30 |
| Control | 9 of 10 | 45.4 ± 13.5* | 29, 30, 35-37, 39, 40 |

Example 3. Design and Synthesis of Library of Backbone Cyclic MyD88 Peptides

A library of backbone-to-backbone cyclic peptides with conformational diversity, was designed on the basis of the 7 amino acid BB loop peptide Arg-Asp-Val-Leu-Pro-Gly-Thr (RDVLPGT, SEQ ID NO: 1) from MyD88 that is proposed to disrupt MyD88 dimerization. The library, represented by Formula IV below comprises a Glycine building unit in the position of the original Proline residue, a second Glycine building unit connected to the Arginine residue and a Tryptophan residue at the N-terminus. All the peptides in the library have the parent sequence and they differ from each other in the bridge size and bridge chemistry. Each of the Gly building units have a bridging arm comprising 2, 3, 4 or 6 methylene groups and a terminal amine group. The two amine groups are connected to form urea bond.

Formula IV

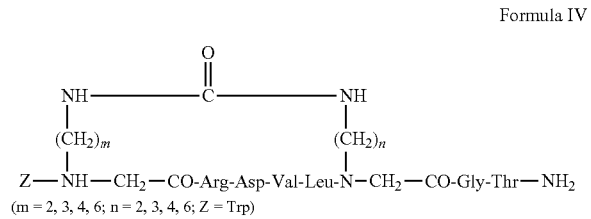

(m = 2, 3, 4, 6; n = 2, 3, 4, 6; Z = Trp)

Figure 3:
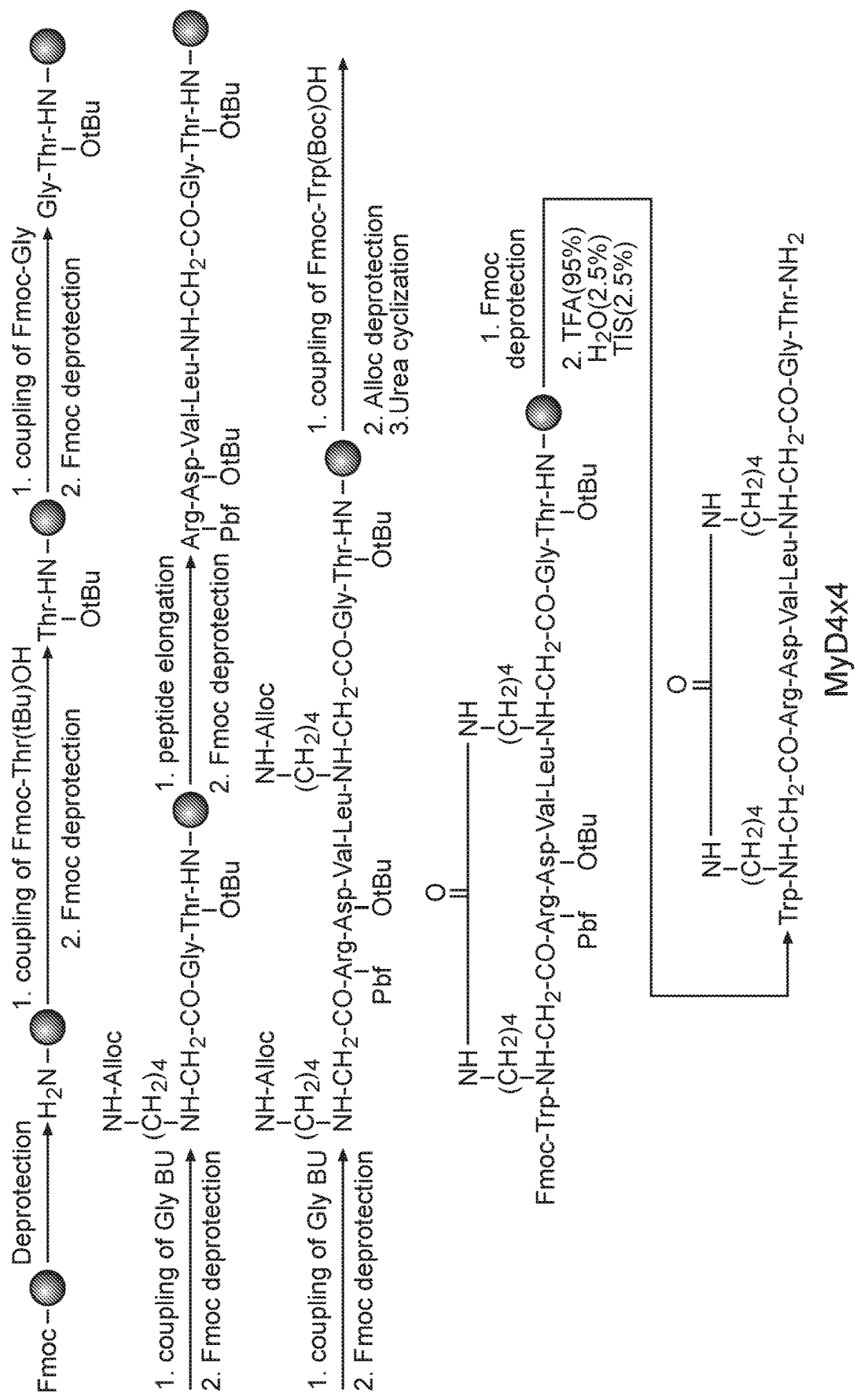
FIG. 3. Synthesis scheme of a representative backbone cyclic peptide library using solid phase peptide synthesis.

The library was synthesized using solid phase peptide synthesis as described in FIG. 3.

Figure 4:
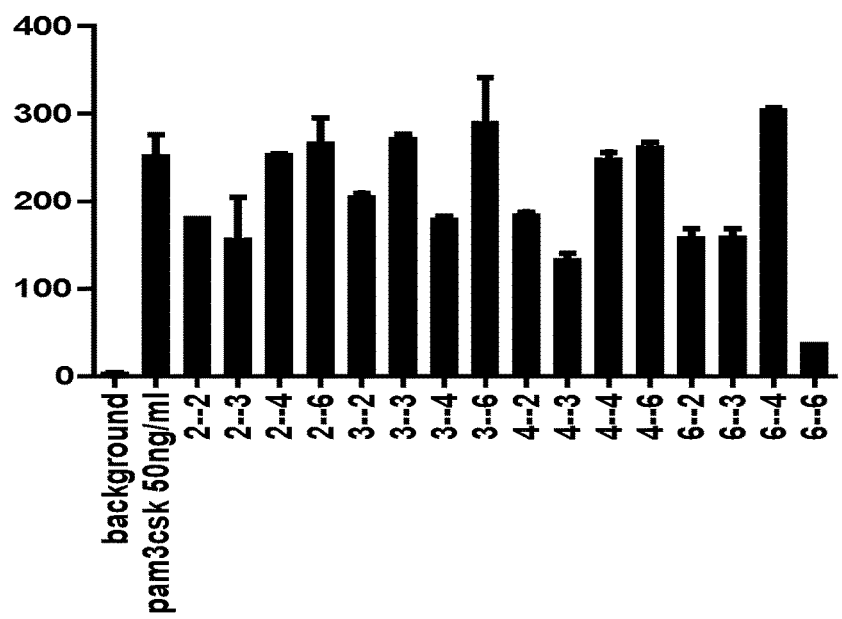
FIG. 4. Screening results of the peptide library of 16 compounds. Human macrophage U937 cells were stimulated with PAM3csk overnight in the absence or presence of each of the cyclic peptides. Human TNFα levels in the supernatants were determined by ELISA. levels in the supernatants were determined by ELISA.

Example 4. Screening of the Cyclic Peptide Library for Inhibition of MyD88-Dependent Signaling The backbone cyclic library of 16 compounds synthesized in Example 3 was screened for inhibition of MyD88-dependent signaling through innate immune receptors employing the human macrophage cell line U937. This cell line displays exquisite sensitivity to stimulation using the TLR2 lipopeptide agonist PAM3Csk. As demonstrated in FIG. 4, the backbone cyclic compound containing a 6×6 bridge (m=6, n=6 in Formula IV) showed greatest MyD88 inhibitory activity represented by a reduction in TNFα production in response to TLR2 activation (a MyD88-dependent pathway). The concentration of the cyclic peptides in the library was estimated to be 2-4 µM.

Figure 5:
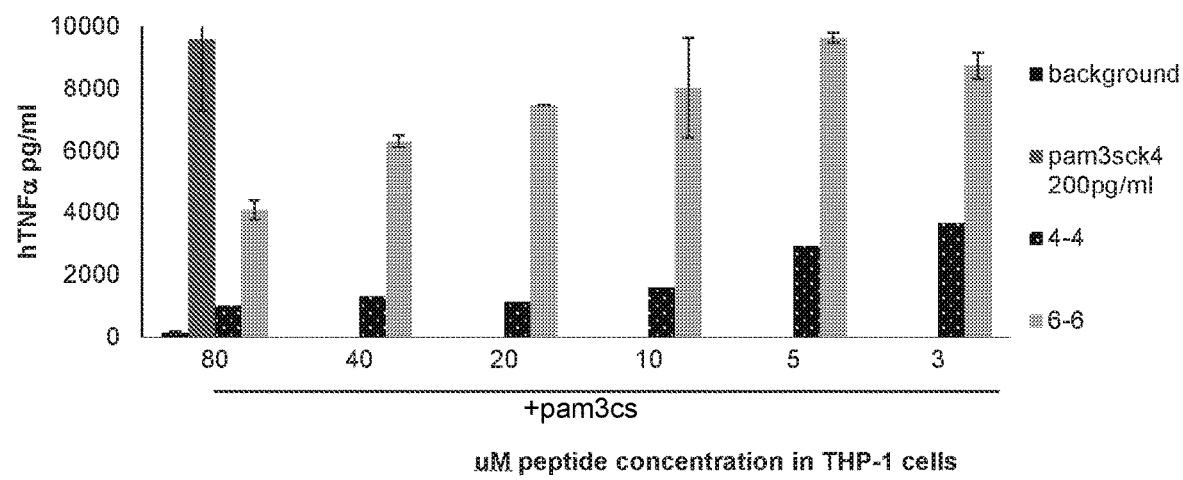
FIG. 5. Human monocytic THP-1 cells were differentiated to macrophages and were stimulated with PAM3csk overnight in the absence or presence of the cyclic 4-carbon bridge peptide or 6-carbon bridge peptide. TNFα levels in the supernatants were determined by ELISA.

Larger quantities of two cyclic peptides, the 6×6 bridge peptide (m=6, n=6 in Formula IV), that exhibited highest activity in the screen, and the 4×4 carbon bridge peptide (m=4, n=4 in Formula IV) were then synthesized. The 4×4 carbon bridge peptide was chosen since it demonstrated intermediate activity in the screen, and previous evidence from other peptide libraries suggested that the 4-carbon bridge presents an advantageous structure. Both cyclic peptides were synthesized with the addition of a tryptophan group to the N-terminus to enable accurate quantification of the molecules. As depicted in FIG. 5, both peptides inhibited the human macrophage production of TNFα in response to stimulation. Surprisingly, the 4×4 bridge peptide outperformed the 6-carbon bridge peptide, suggesting that the concentrations of these peptides in the initial library screen were not equivalent.

Example 5. Specificity of MyD88 Inhibition by the Backbone Cyclic Peptide 4×4MyDI Lead compounds were further tested in vitro to confirm the specificity of the inhibition. A fluorescence-based in vitro activity assay that determines the degree of activation of the transcription factor NFκB was established. In this assay, cells are treated with either TNFα or IL-1b, both inflammatory cytokines that activate NFκB. Upon activation, the p65 unit of the NFκB transcription factor re-locates from the cytoplasm to the nucleus. Using fluorescently-tagged antibodies to p65, the cytoplasmic vs. nuclear localization of the factor is determined. Importantly, since the signaling of IL-1b, but not TNFα, is dependent on MyD88, this assay can establish the specificity of the inhibition achieved using the lead compounds.

Figure 6A:
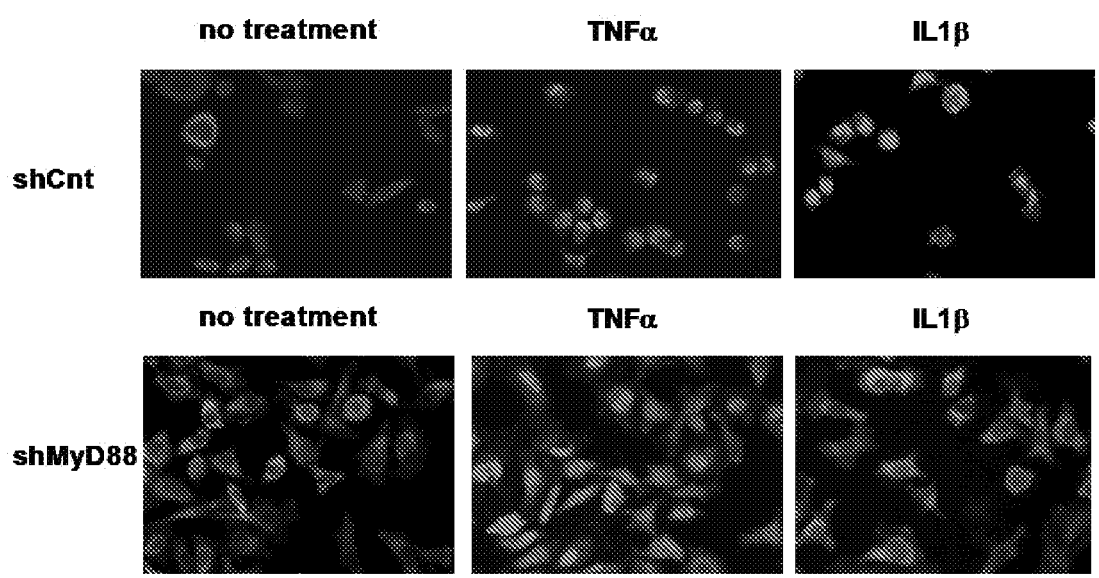
FIG. 6. HeLa assay showing specificity of MyD88 inhibition. HeLa cells were stimulated with recombinant TNFα or IL-1β and NFkB localization was determined with anti-p65 conjugated to rhodamine. The percent of cells with nuclear localization was determined and is shown in the bar graphs on the right. 6A: Top row, HeLa cells transduced with control shRNA. Second row, shRNA knock-down of MyD88. 6B: Top row, HeLa cells treated with MyD88 inhibitor linear peptide. Bottom row, HeLa cells treated with scrambled control version of the MyD88 inhibitor linear peptide (SEQ ID NO: 5). Each row shows no treatment, stimulation with TNFα (no MyD88 involvement in signaling pathway), and treatment with IL-1β (MyD88 dependent signaling).

Cells were activated with either IL-1β (the signaling of the IL-1 receptor is dependent on MyD88), or with TNFα (signaling of its receptor is independent of MyD88). The activation was measured by the translocation of NFκB from the cytoplasm to the nucleus. As a positive control, a stable MyD88 knock-down cell line was established using lentiviral encoded shRNA. FIG. 6A shows that the knock-down of MyD88 using shRNA specifically blocks IL-1β signaling without affecting NFκB activation in response to TNFα (control shRNA cells vs. shRNA to MyD88). Using this system the linear MyD88 inhibitor 7-mer peptide demonstrates specificity (FIG. 6B, linear peptide vs. scrambled peptide control).

Figure 8:
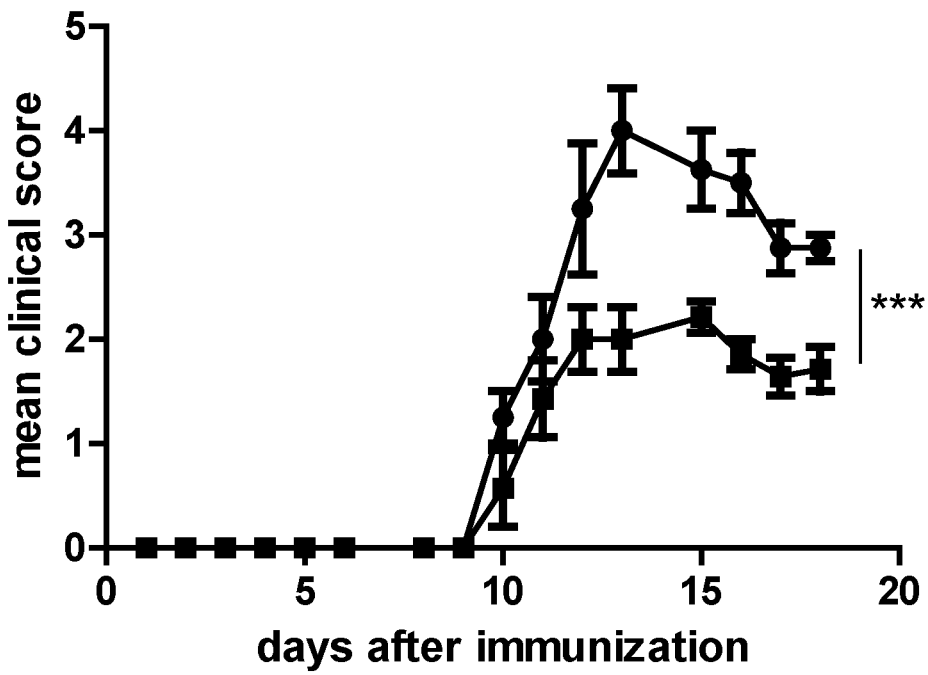
FIG. 8. 4×4MyDI lowers disease in mouse EAE model. Mice were immunized with MOG35-55/CFA with PTX administration at day 0 and at 48 h. Groups of mice were treated with 4×4MyDI (squares, n=7) or PBS as control (circles, n=4) from day 0, three times a week. Differences in cumulative disease score show that mice treated with 4×4MyDI showed significantly (***P<0.0001 by 2 way analysis of variance) lower disease scores and a better rate of survival.

Using the same system, when cells were treated with the backbone cyclic peptide 4×4MyDI, activation by IL-1β was blocked, however when treated with TNFα the activation was not inhibited. This experiment demonstrates that the 4×4MyDI is a specific inhibitor (FIG. 8).

Figure 6B:
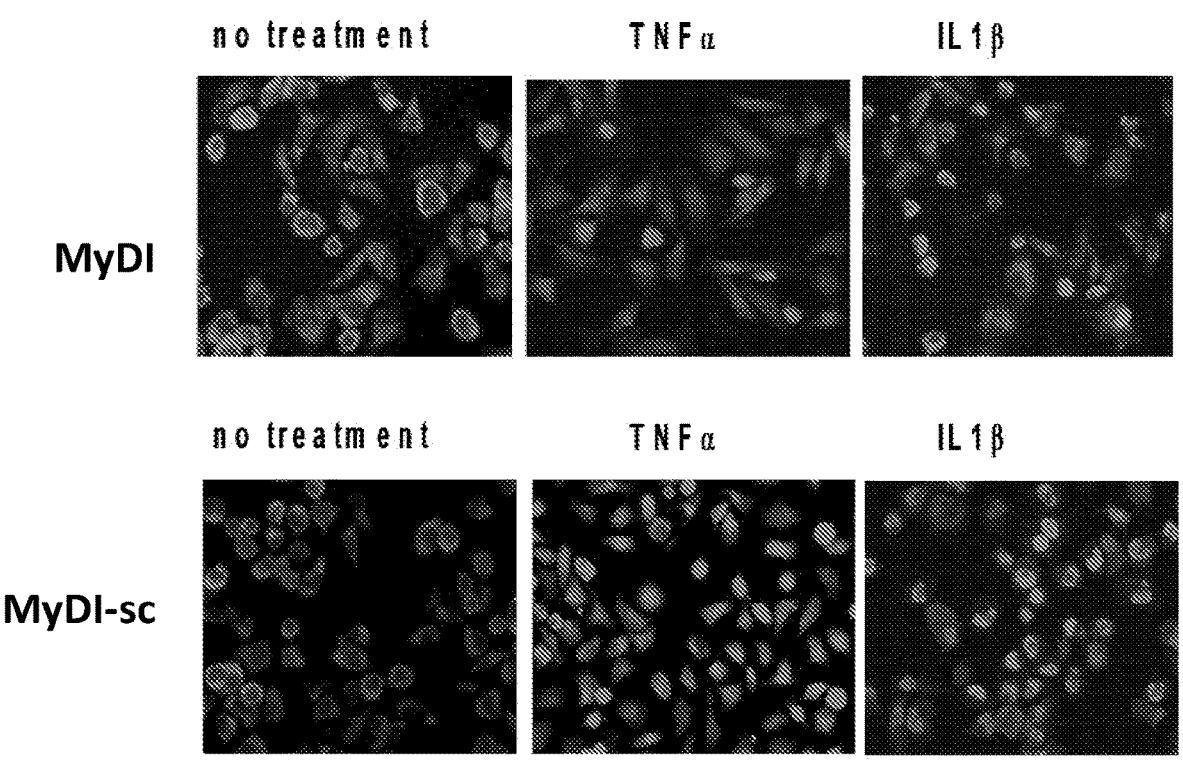
Figure 7:
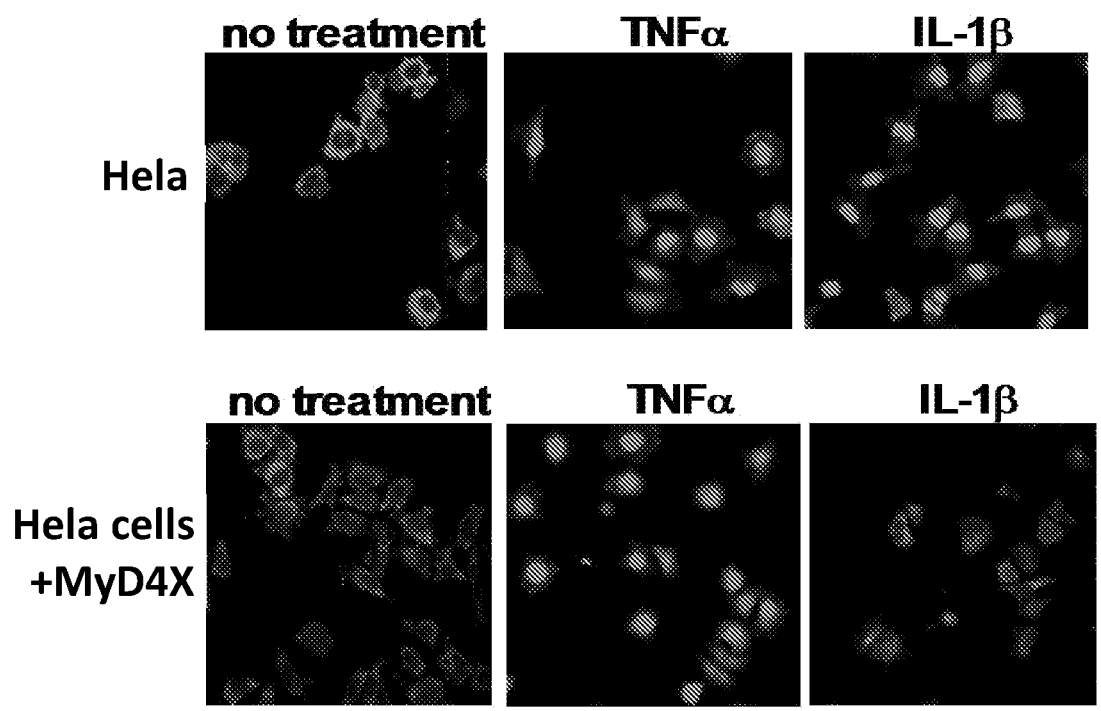
FIG. 7. HeLa assay showing specificity of MyD88 inhibition by 4×4MyDI. HeLa cells were stimulated with recombinant TNFα or IL-1b and NFkB localization was determined with anti-p65 conjugated to rhodamine. The percent of cells with nuclear localization was determined, and is shown in the bar graphs on the right. Top row, HeLa cells with no pre-treatment. Second row, HeLa cells pre-treated for 30 min with the backbone cyclic 4×4MyDI compound.

The quantified results of FIGS. 6A, 6B and 7 are summarized in Table 2.

TABLE 2

Percent p65 nuclear translocation in HeLa cells

| Tested cells/compound | No stimulation | TNFα | IL-1β |
|---|---|---|---|
| Control cells (shCnt) | 0 | 95 | 91 |
| shMyD88 cells (shMyD88) | 0 | 90 | 6 |
| Hela Cells with MyDI | 0 | 75 | 20 |
| Hela Cells with MyDI scrambled | 0 | 90 | 91 |
| Hela cells | 0 | 95 | 100 |
| Hela cells with 4 × 4 peptide | 0 | 97 | 27 |

Example 6. Animal Models

Following bioactivity characterization in vitro, the lead compound was evaluated for efficacy using the in vivo murine $MOG_{35-55}$-induced EAE model of multiple sclerosis. In this model, mice are immunized with $MOG_{35-55}$/CFA, and treated with pertussis toxin at two time points (the day of immunization and 48 h later). Typically, mice develop progressive paralysis starting at around day 8-10. One dose of the 4×4MyDI compound was tested using two treatment schedules, either starting treatment on the day of immunization with MOG35-55 (MEVGWYRSPFSRVVH-LYRNGK, SEQ ID NO: 4), or starting treatment on day 7 when the immune response is well underway and clinical symptoms are about to start. In both cases the mice were treated by i.p. injections of the compound diluted in PBS, three times a week at 4 mg/Kg. As shown in FIG. 8, a significant reduction in disease severity was observed in the group treated with the backbone cyclic peptide 4×4MyDI from the day of immunization against $MOG_{35-55}$. In contrast, mice treated with 4×4MyDI from day 7 behaved similarly to the control group, suggesting that in order to be effective the 4×4MyDI must be administered prior to full activation of the immune response to the self-antigen. While this result may seem discouraging, patients with multiple sclerosis suffer from flare-ups of disease activity interspersed with relatively quiescent periods, at least for the initial years of the disease. This clinical behavior supports the notion that the MyD88 inhibitor can exert efficacy when administered during a quiescent period as a prevention of further flare-ups.

Figure 15:
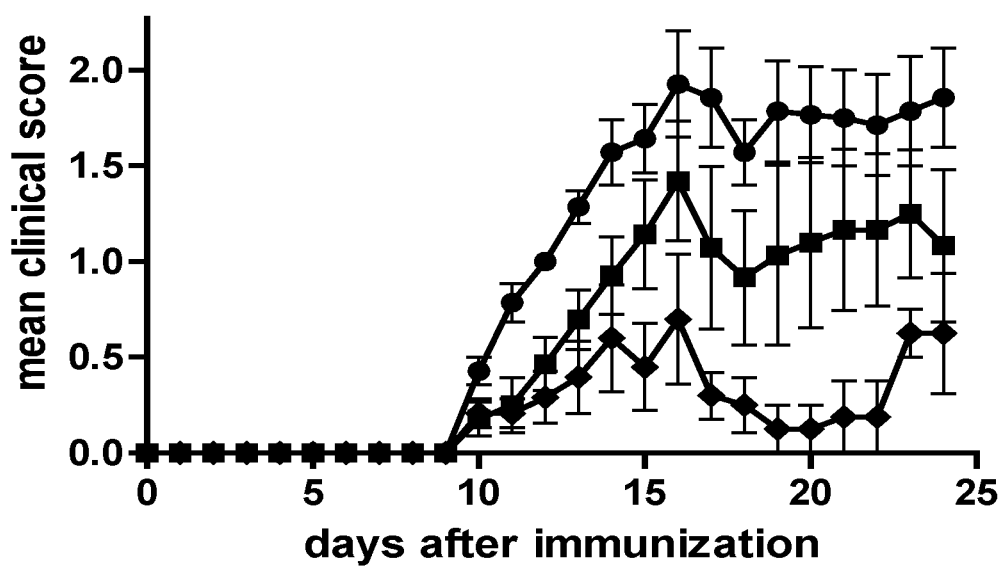
FIG. 15. 4×4MyDI reduces severity of EAE. C57BL/6 mice were immunized with MOG35-55/CFA and administered pertussis toxin on day zero and after 48 h. Groups of mice were treated with 4×4MyDI at 4 mg/kg from day zero, three times a week, for a total of 9 treatments (squares, n=7) or an identical volume of PBS as control, using the same schedule of administration (circles, n=7). An additional group of mice was treated with 4×4MyDI at 40 mg/kg on day zero and after 48 h with no further treatments (rhombuses, n=6). Clinical disease was scored daily. ***P<0.0001, 2-way ANOVA.

The 4×4MyDI was further tested in this model using only two injections of a higher dose of the inhibitor. As shown in FIG. 15, the original dose of 4 mg/Kg administered three times a week starting at day 0 significantly reduced disease severity. Furthermore, administration of a dose of 40 mg/Kg on day zero and day three only, reduced disease severity even further.

Figure 16A:
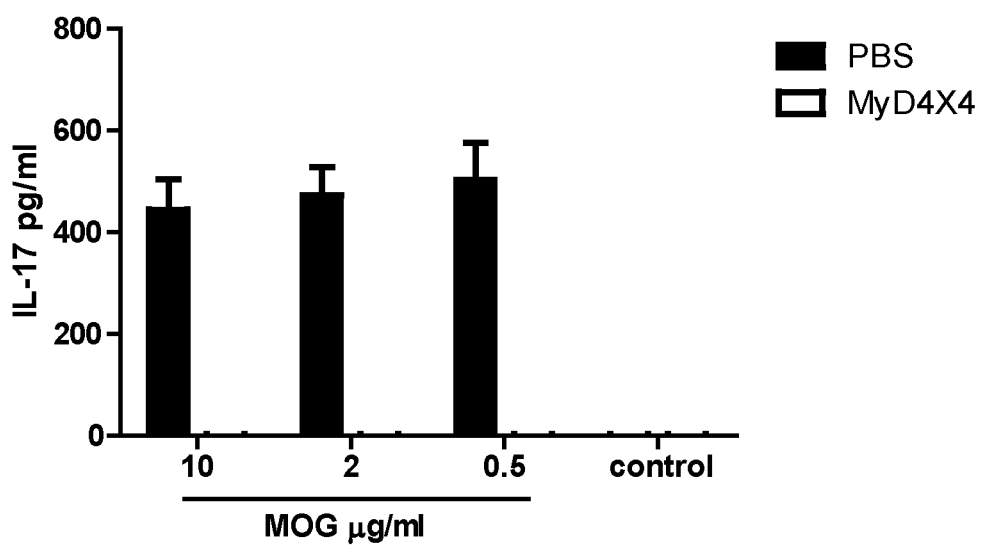
FIGS. 16A and 16B. inhibition of IFNγ and IL-17 secretion in 4×4MyDI treated mice. C57BL/6 mice were immunized with MOG35-55/CFA and administered pertussis toxin on day zero and after 48 h. Groups of mice were treated with 4×4MyDI at 4 mg/kg from day zero, three times a week, and animals were sacrificed on day 11 after immunization. Control mice were treated with an equal volume of PBS using the same schedule of administration. Single cell suspensions from draining lymph nodes were stimulated with different concentrations of MOG35-55 peptide (SEQ ID NO: 4) for three days and supernatants were collected for analysis of cytokines by ELISA.
Figure 16B:
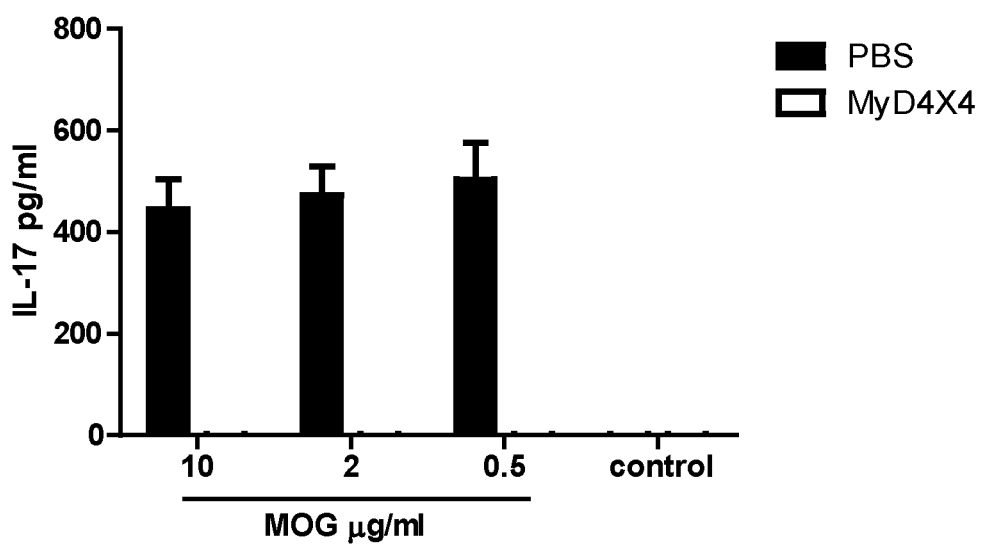

The mechanism of action in vivo was demonstrated by immunizing mice with MOG35-55/CFA and treating them with the 4×4MyDI three times per week at 4 mg/Kg until day 11 at which time the mice were sacrificed and the cytokine response of draining lymph node cells activated with the self-antigen MOG35-55 was tested. As shown in FIGS. 16A and 16B, treatment with the inhibitor compound in vivo led to a complete inhibition of IFNγ (FIG. 16A) and IL-17 (FIG. 16B), produced by T cells responding to the self-antigen MOG35-55. Of note, IFNγ and IL-17 are considered pro-inflammatory cytokines that are highly detrimental in the autoimmune process.

Further animal testing in models of EAE and other models of human disease are performed. Specifically, the relapsing-remitting EAE model induced by PLP immunization in SJL mice and the model of progressive EAE in NOD mice are employed. Additional models of autoimmune and inflammatory diseases are employed such as the collagen induced arthritis model, DSS-induced colitis, and models of sepsis induced by TLR ligands that signal through MyD88. In addition, models of cancer where MyD88 is implicated are employed (Kfoury A et al, Curr Opin Oncol. 2014 January; 26(1):86-91.

Example 7. Binding of 4×4MyD and Inhibition of Dimerization

Figure 9:
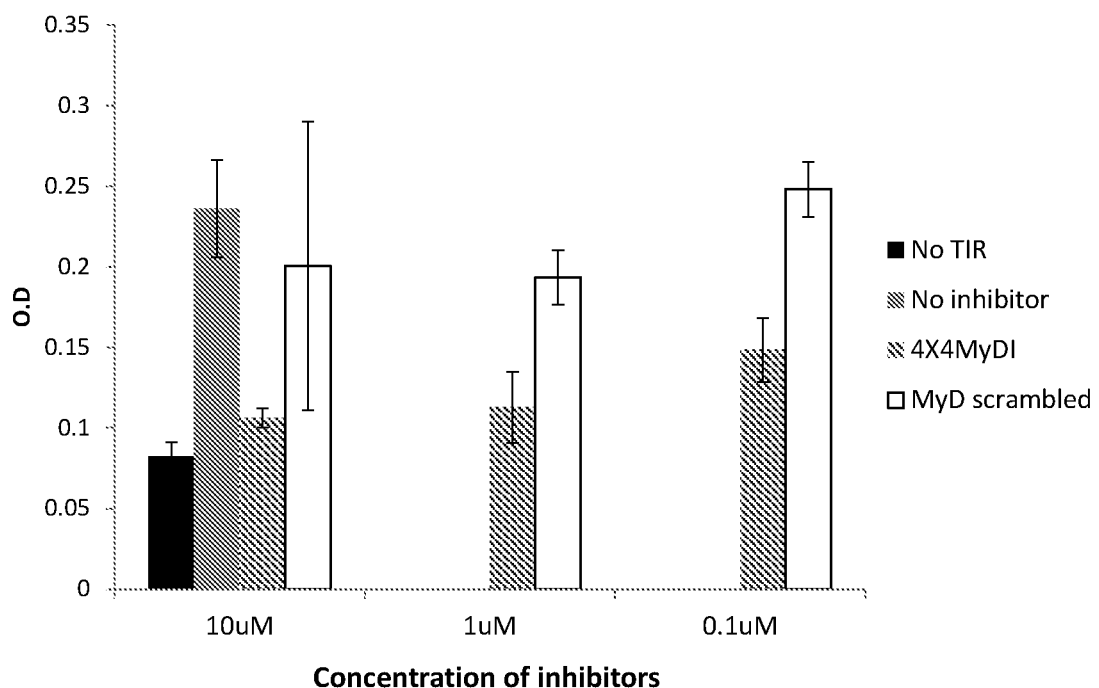
FIG. 9. 4×4MyDI binds to the BB loop region of the MyD88 TIR domain. A 96 well plate was coated with recombinant MyD88 (8 μg/ml) in coating buffer vs. buffer alone, and wells were blocked with 1% BSA. Biotinylated linear peptide was added to all wells (125 μg/ml) followed by streptavidin-HRP and substrate. The signal of linear peptide bound to its target was inhibited by incubation with the 4×4MyDI (*P<0.05) but not by incubation with the scrambled version of the linear peptide (SEQ ID NO: 5).

The ability of the 4×4MyDI compound to bind to the target region (the BB loop) of the MyD88 TIR domain, was evaluated using a newly-designed assay. For this goal a competition assay was established that tests the ability of the 4×4MyDI compound to prevent the binding of the biotinylated linear BB loop peptide to the MyD88 TIR domain. The MyD88 TIR domain was produced as a recombinant protein fused to the SUMO3 protein (Accession # NP_008867), purified, and attached to a 96 well plate. Binding of biotinylated RDVLPGT (SEQ. ID NO: 1) peptide was detected using streptavidin conjugated to horse radish peroxidase (HRP) followed by the addition of HRP substrate. Incubation with different concentrations of 4×4MyDI competitively inhibited the binding of the biotinylated peptide to the MyD88 TIR domain, as shown in FIG. 9. The scrambled version of the linear peptide (MyD scrambled) did not inhibit binding of the biotinylated peptide at any of the concentrations tested, as expected.

Adaptation of a known (Loiarro M. et al, J Biol Chem. 2005 Apr. 22; 280(16):15809-14) assay was used to show inhibition of myd88 dimerization. The assay is based on co-transfection of two tagged versions of full length Myd88—HA-MyD88 and Flag-Myd88. The HA-Myd88 can be immunoprecipitated and the protein recovered analyzed by western blot with an antibody to the flag tagged MyD88. The amount of flag present reflects the extent of dimerization.

Figure 10:
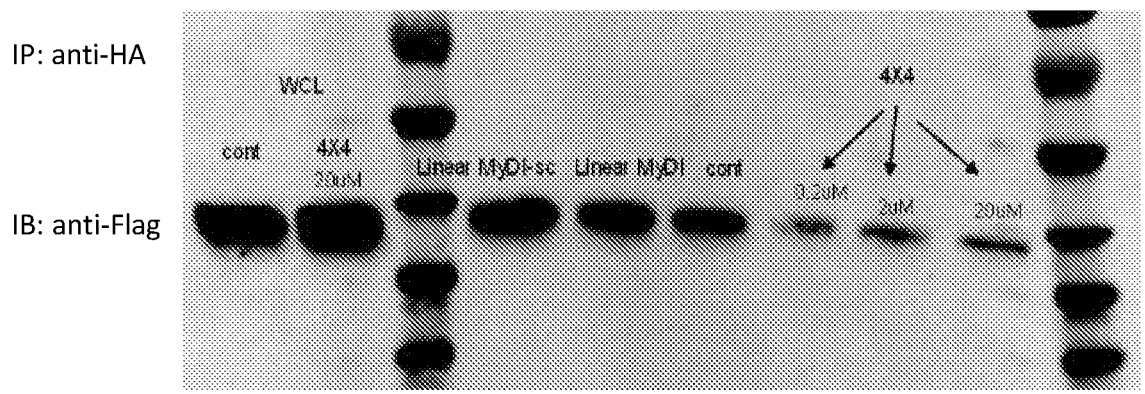
FIG. 10. 4×4MyDI blocks MyD88 dimerization. HEK293 cells were transfected with two plasmids, one encoding HA-MyD88 and the other encoding FLAG-MyD88 and after 48 hours the cells were either untreated (cont) or treated with 20 μM of the linear MyDI peptide, the scrambled version of the linear MyDI peptide (SEQ ID NO: 5,), or the 4×4MyDI at 20, 2, or 0.2 μM. After 3 h of treatment, cells were stimulated with recombinant human IL-1 (20 ng/ml) for 30 min and then lysed. Whole cell lysates (WCL) were immunoprecipitated with anti-HA beads (Thermo-Scientific) for 30 min and proteins were eluted with glycine Ph 2.0, neutralized, and loaded on an acrylamide gel for analysis. Proteins were transferred to nitrocellulose and the amount of Flag-MyD88 that co-precipitated with HA-MyD88 was detected by immunoblotting (IB) with anti-Flag antibody. WCL were also analyzed to demonstrate at least equivalent Flag-MyD88 expression in the cells treated with 4×4MyDI compared to control.

TLR and IL-1 receptor signaling proceeds through a multimeric protein signaling complex (the "Myddosome") that is initiated by MyD88 homodimerization. According to the TIR domain crystal structure, the dimerization interface involves the MyD88 BB loop of the TIR domain, and the linear RDVLPGT peptide (SEQ ID NO: 1) interferes with MyD88 dimerization by competitively inhibiting TIR-TIR dimerization. To determine the potential for the 4×4MyDI to inhibit dimerization of MyD88, HEK cells were co-transfected with constructs encoding HA-tagged full length MyD88 and Flag-tagged full length MyD88. Following co-transfection, cells were treated with linear and cyclic MyD88 inhibitors vs. controls, and then stimulated with IL-1 (to drive Myddosome assembly). Cells were then lysed and HA-MyD88 was immunoprecipitated from the whole cell lysates using anti-HA covalently linked to magnetic beads. Immunoprecipitated protein was eluted and analyzed by immunoblot using an antibody to Flag. As shown in FIG. 10, anti-flag detects a band at the expected MW of MyD88 (36-38 KD) in the whole cell lysates (WCL) and in the protein eluate from the anti-HA immunoprecipitates. The appearance of the band in the immunoprecipitate represents the Flag-MyD88 that dimerized with HA-MyD88 and was therefore brought down together with the HA-MyD88. FIG. 10 shows that treating the cells with the 4×4MyDI (denoted 4×4 in the figure) dramatically reduces the dimerization of MyD88 following IL-1 stimulation at all concentrations tested. As shown in the figure, the 4×4MyDI compound reduced MyD88 dimerization to a much greater degree than the linear BB loop peptide. WCL prepared from control cells and those treated with the highest concentration of 4×4MyDI show that the transfection efficiency was similar in the untreated and treated cells. Nevertheless, the 4×4MyDI prevented MyD88 dimerization.

Example 8. The Permeability Properties of 4×4MyDI

Figure 11:
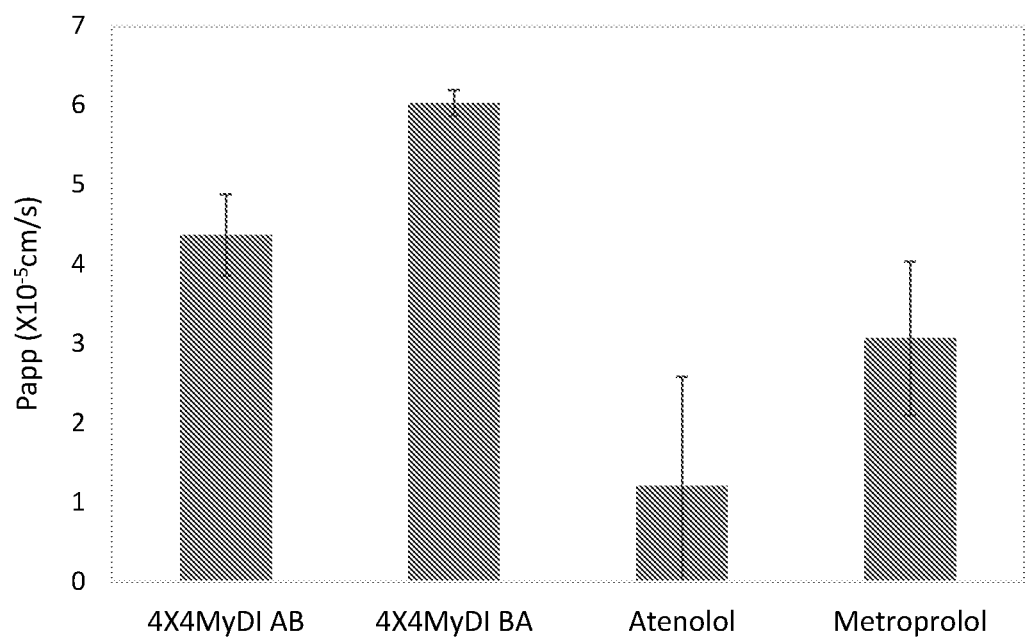
FIG. 11. $P_{app}$ of several compounds in the CaCO-2 model: 4×4MyDI (AB and BA), Atenolol and Metoprolol FIG. 12. $P_{app}$ of 4×4MyDI in the PAMPA model in comparison to metoprolol.

The investigation of the permeability of 4×4MyDI through CaCO-2 monolayer includes using two main control groups, Atenolol and Metoprolol that show passive paracellular and trans-cellular permeability, respectively. The CaCO-2 model allows investigating the mechanism of absorption, so the permeability from apical to basolateral membranes (AB) can be measured to evaluate the total permeability. The permeability from basolateral to apical membranes (BA) can also be measured and compared to AB P apparent (Papp) to determine if the absorption is though passive diffusion, active transporters or if there is involvement of efflux systems. As shown in FIG. 11, the Papp value of 4×4MyDI-AB is higher than metoprolol so the permeability of 4×4MyDI is surprisingly high in comparison to metoprolol, suggesting trans-cellular permeability mechanism. Moreover, the BA Papp value is also high, suggesting the involvement of efflux system that transports 4×4MyDI from the cytosol through the apical membrane to the lumen.

Figure 12:
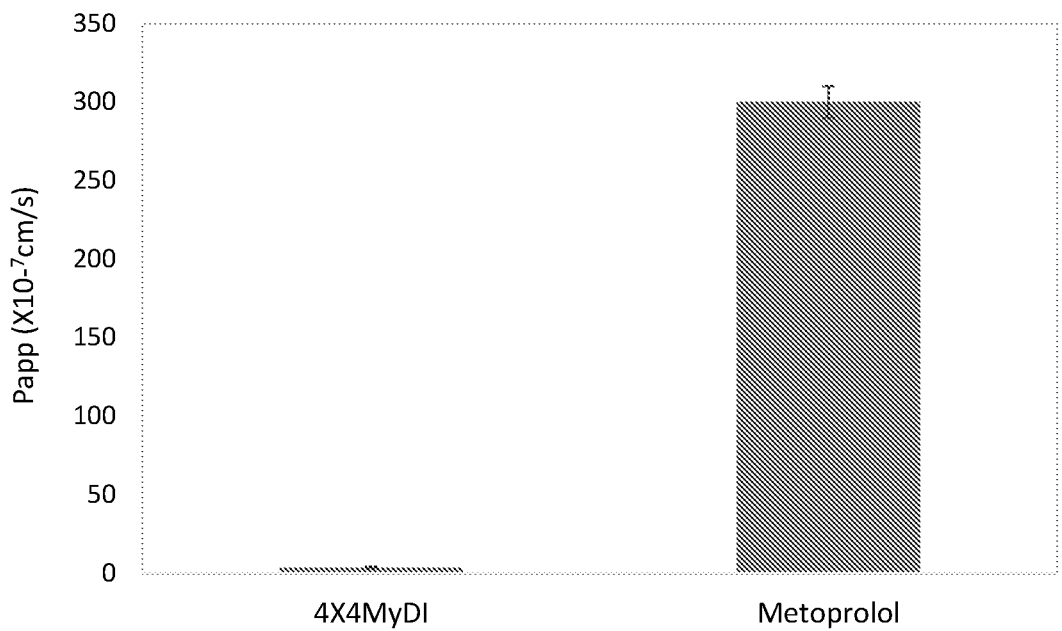

The Parallel Artificial Membrane Permeability Assay (PAMPA) is another permeability model that is used for investigating the permeability mechanism of new molecules. This model does not include cells, so it is used to evaluate the permeability of molecules through a lipid layer by passive diffusion. The results shown in FIG. 12 emphasize that 4×4MyDI does not diffuse well through a lipid layer, in comparison to metoprolol (standard compound for good passive diffusion). This result suggests that the mechanism of permeability of 4×4MyDI involves transport system that exists in cellular models only. This mechanism of intestinal permeability was substantiated by further permeability investigations of 4×4MyDI in Caco2 monolayer model were the permeability rate for basolateral to apical side (BtoA) through the enterocytes was significantly higher than the AtoB kinetics (FIG. 12). These findings regarding the mechanism of 4×4MyDI-membrane behavior are of great importance for the development of 4×4MyDI into a clinically important medication, and provide indications for the proper pharmaceutical delivery system that would be optimal for this active compound.

Example 9. Future Target Molecules Based on the Lead

The importance of additional moieties to enhance cell penetration is further evaluated. Addition of a cell penetration moiety greatly enhances the activity, as demonstrated by comparison of the linear MyD88 inhibitor 7-mer peptide to an identical peptide synthesized with a myristoyl group at the N-terminus. Myristoylation has been shown to enhance cell penetration of peptides and small molecules, and in the case of the linear peptide, addition of the myristoyl group significantly enhances activity without affecting peptide stability. Therefore, backbone cyclic peptides with addition of a myristoyl group or other moieties designed to enhance cell penetration are also synthesized and tested for binding, inhibition, stability and permeability. Some of these compounds are described below:

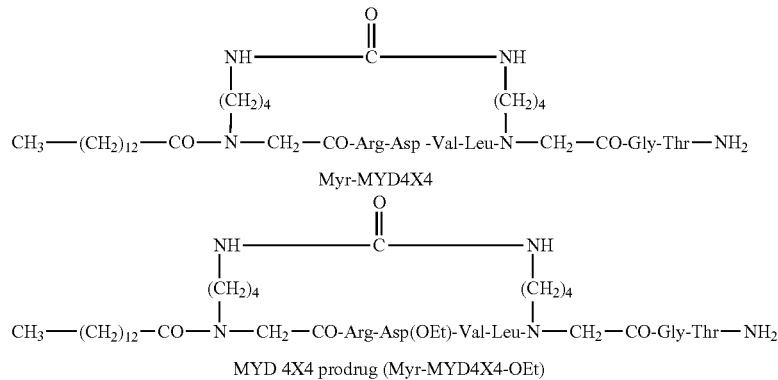

Example 10. Inhibition of MyD88 Activity by 4×4MyDI and Myr-4×4MyDI

Figure 13:
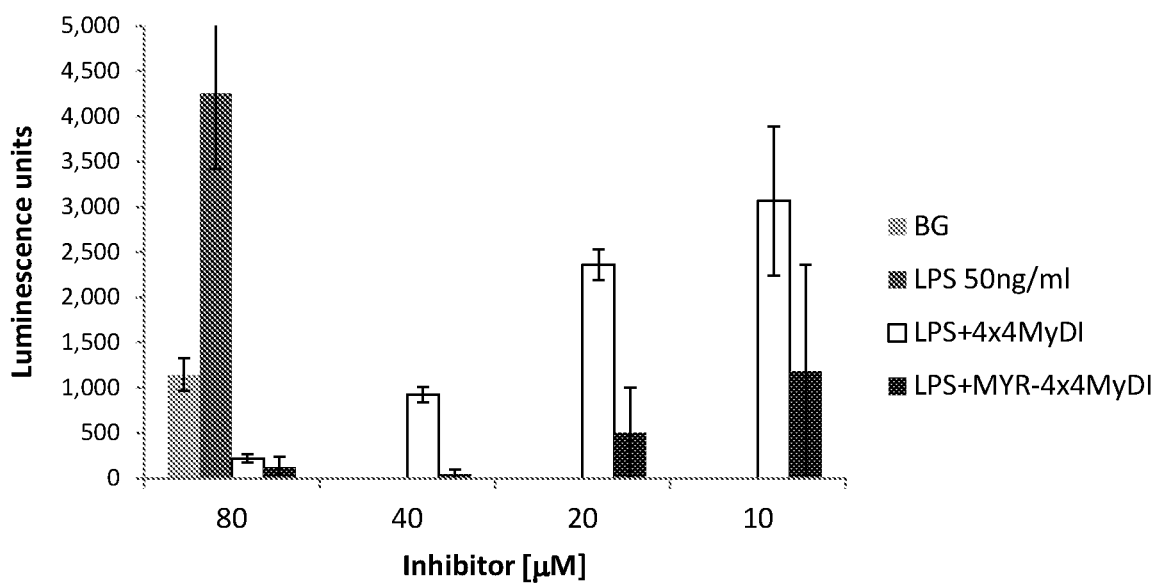
FIG. 13. 4×4MyDI and Myr4×4MyDI block NFkB induction in response to LPS stimulation of RAW 264.7 NFkB-luc cells. RAW 264.7 murine macrophages were transfected with an NFkB-luciferase reporter gene and stimulated with LPS in the absence or presence of increasing concentrations of the inhibitors. After 4 hours cells were lysed and luminescence was recorded using a Tecan plate reader. BG denotes background.

Inhibition of MyD88 activity by 4×4MyDI and Myr-4×4MyDI was demonstrated in an additional cellular assay. In this assay the mouse macrophage RAW264.7 cell line is transfected with an NFkB-luciferase reporter construct and then cells are stimulated by exposure to bacterial LPS and light emission is measured after addition of luciferase substrate. As shown in FIG. 13, the inhibitors block NFkB activation in a dose dependent manner, with Myr-4×4MyDI demonstrating greater activity than the 4×4MyDI compound.

Figure 14A:
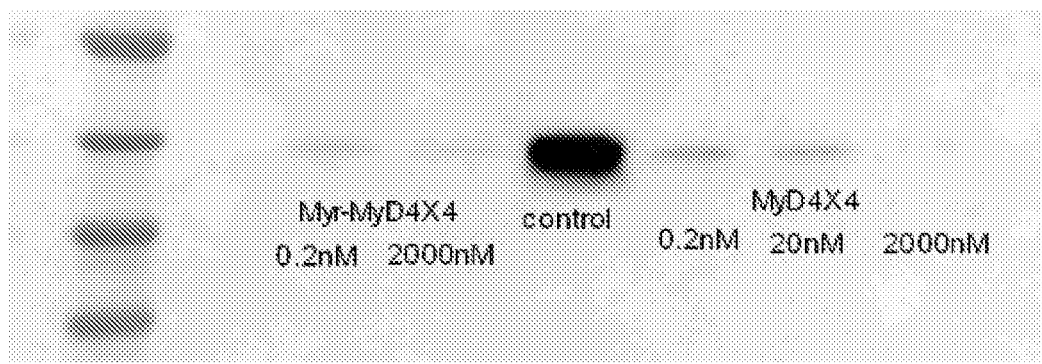
FIGS. 14A and 14B. Myr-4×4MyDI and 4×4MyDI block MyD88 dimerization. (15A) Anti-Flag WB. HEK293 cells were transfected with two plasmids, one encoding HA-MyD88 and the other encoding FLAG-MyD88 and after 48 hours the cells were either untreated (control) or treated with Myr-4×4MyDI (at 0.2 or 2000 nM), or 4×4MyDI (at 0.2, 20, or 2000 nM). After 3 h of treatment, cells were stimulated with recombinant human IL-1 (20 ng/ml) for 30 min and then lysed. WCL were immunoprecipitated with anti-HA beads (Thermo-Scientific) for 30 min and proteins were eluted with glycine Ph 2.0, neutralized, and loaded on an acrylamide gel for analysis. Proteins were transferred to nitrocellulose and the amount of FLAG-MyD88 that co-precipitated with HA-MyD88 was detected by immunoblotting (IB) with anti-FLAG antibody. (15B) Percent inhibition of co-immunoprecipitation was calculated by comparing densitometry of bands in the treated lanes to control. WCL of all samples were also analyzed to demonstrate at least equivalent FLAG-MyD88 expression in the cells treated with Myr-4×4MyDI or 4×4MyDI compared to control cells.
Figure 14B:
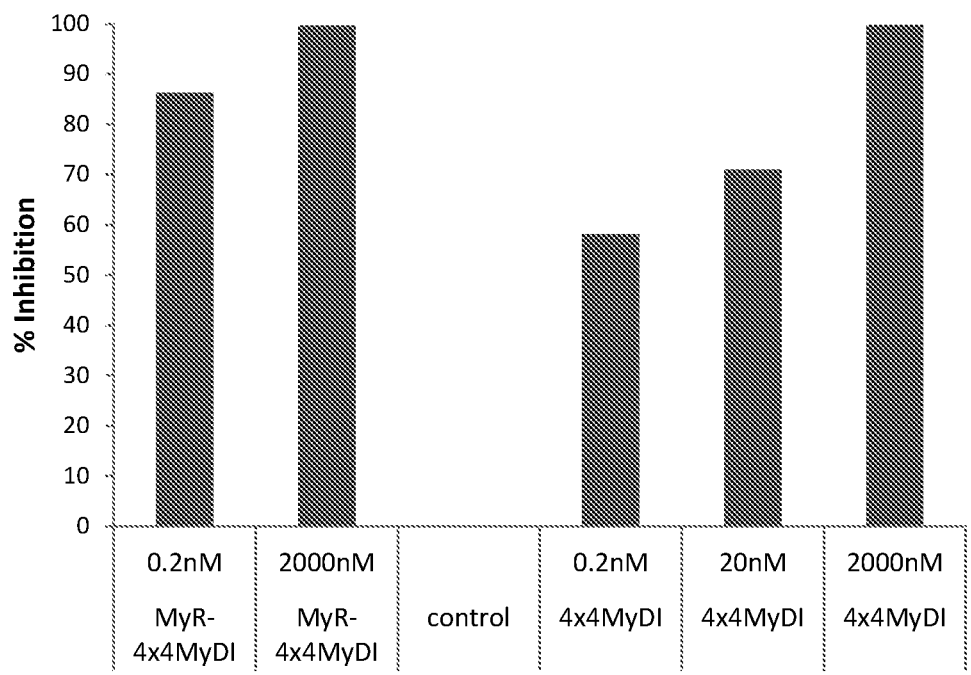

As in example 7 (FIG. 10), the ability of Myr-4×4MyDI to block MyD88 dimerization was evidenced by its ability to inhibit the co-immunoprecipitation of Flag-MyD88 with HA-MyD88. As shown in FIGS. 14A and 14B, Myr-4×4MyDI was at least as active as 4×4MyDI in this assay.

Example 11. Metabolic Stability of 4×4MyDI

Figure 17A:
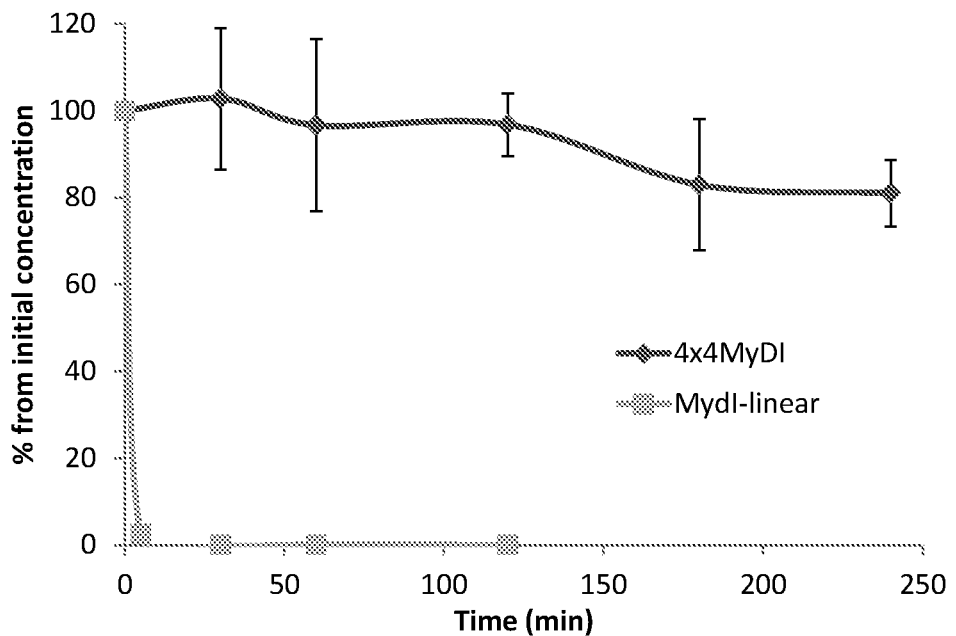
FIG. 17A shows IFNγ levels and FIG. 17B IL-17 levels.
Figure 17B:
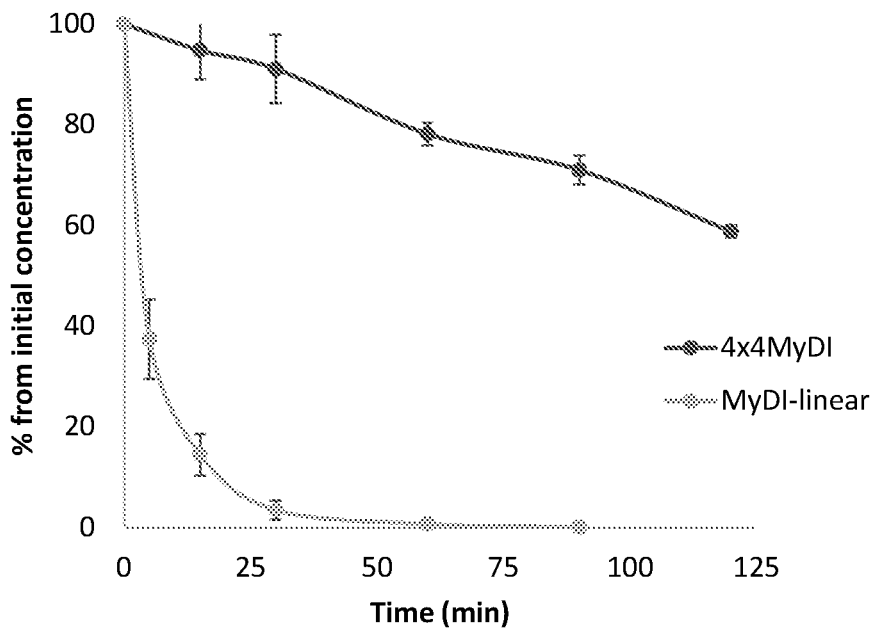

Peptide backbone cyclization confers metabolic stability on peptides that are inherently susceptible to degradation by proteases. To demonstrate this advantage, the linear heptameric peptide RDVLPGT (SEQ ID NO: 1), and the backbone cyclized 4×4MyDI were incubated in plasma over time and the amount of the compounds was tested by quantitative HPLC and compared to the original amount. As shown in FIG. 17A, the linear peptide disappears rapidly in plasma, as expected. In contrast, the 4×4MyDI is completely stable over the first two hours of this assay, and then decreases by only 20% over the following two hours. The stability of the compounds was then tested in plasma enriched with Brush Border Membrane Vesicles (BBMV). This system models the degradative conditions of the intestine. As shown in FIG. 17B, even in these conditions the 4×4MyDI is highly stable and over two hours the decrease is only 40%.

Example 12. 4×4MyDI Blocks Proliferation of Lymphoma Cells Carrying the MyD88L265P Activating Mutation Genomic DNA was prepared from the human lymphoma cell lines OCI-LY3 (MyD88$^{L265P}$) and OCI-LY19 (MyD88$^{WT}$) to confirm the presence of the activating L265P mutation in the OCI-Ly3 cells (and the WT sequence in the OCI-Ly19 cells). The MyD88 region was amplified using the forward and reverse primers GGG ATA TGC TGA ACT AAG TTG CCA C (SEQ ID NO: 7) and GAC GTG TCT GTG AAG TTG GCA TCT C (SEQ ID NO: 8), respectively, as described in Xu, L. et al *Blood* (2013) 121(11): 2051-2058. The PCR product was sequenced to confirm the mutation. As shown in Table 3, the sequence of OCI-Ly3 was consistent with reports, showing a proline at amino acid position 265 in the OCI-Ly3 cells, and the wild-type sequence containing leucine at that position in the Ly19 cells.

Figure 18A:
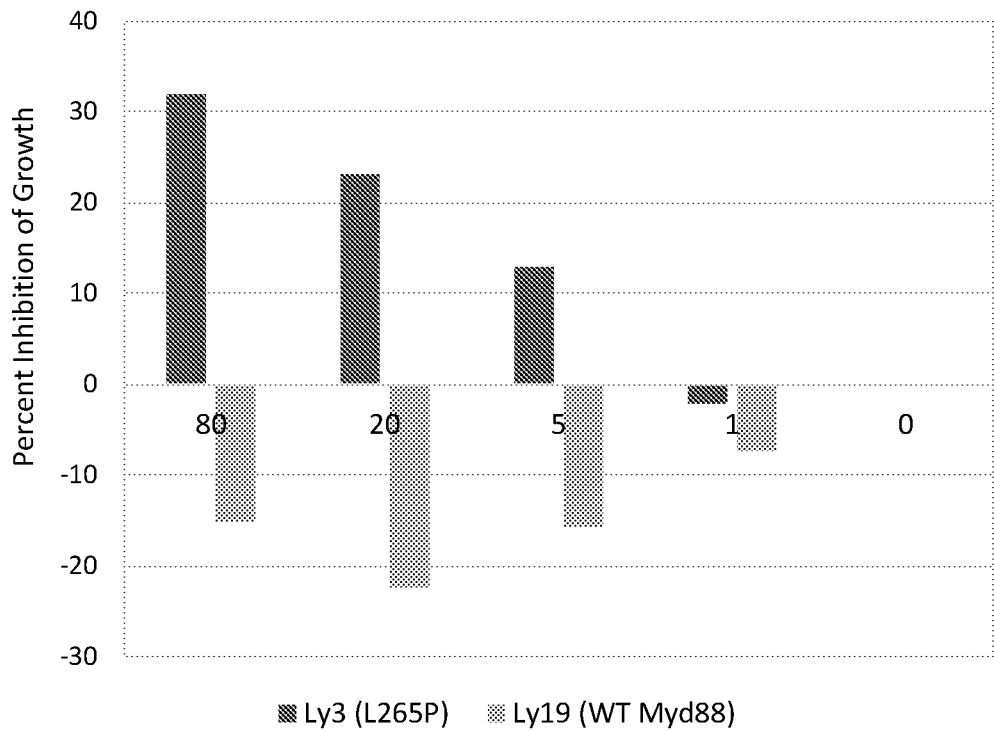
FIGS. 18A and 18B. 4x4MyDI and Myr-4x4MyDI block proliferation of Ly3 lymphoma cells that carry the L265P oncogenic mutation in MyD88. Cell lines OCI-LY3 (MyD88$^{L265P}$) and OCI-LY19 (MyD88$^{WT}$) were grown in RPMI supplemented with 10% FCS. Cells were counted and plated at identical concentrations in triplicate wells of 96 well plates and decreasing concentrations of 4x4MyDI (19A), or Myr-4x4MyDI (19B), was added to the wells. After 48 h cell viability was tested using the Promega CellTiter viability assay according to the manufacturer's instructions. Percent inhibition was calculated as [(1-OD of well with inhibitor/OD of well without inhibitor)*100]. Negative values in A represent enhanced growth in the presence of the inhibitor.
Figure 18B:
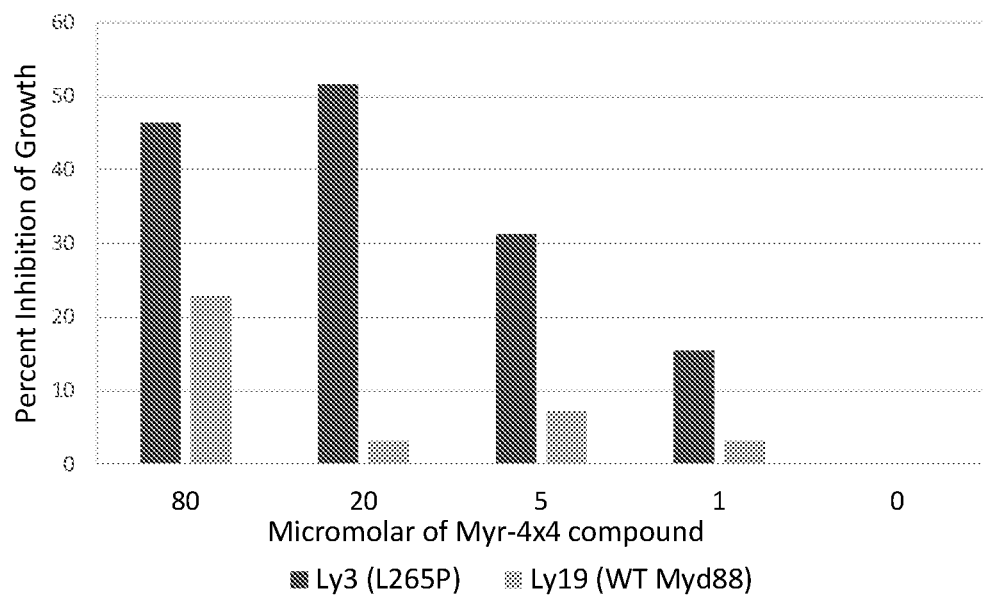

The cell lines were incubated alone or with increasing concentrations of the 4×4MyDI. Proliferation was tested using the Promega CellTiter viability assay according to the manufacurer's instructions. As shown in FIGS. 18A and 18B, the 4×4MyDI compound (19A) and the Myr-4×4MyDI compound (19B) specifically blocked proliferation of the OCI-Ly3 cells that contain the L265P oncogenic mutation in MyD88.

TABLE 3

| Cell Line | Genomic DNA Sequencing result | Amino acid at position 265 |
| --- | --- | --- |
| OCI-Ly3 | CCG | Proline (Pro) |
| OCI-Ly19 | CTG | Leucine (Leu) |

While the present invention has been particularly described, persons skilled in the art will appreciate that many variations and modifications can be made. Therefore, the invention is not to be construed as restricted to the particularly described embodiments, and the scope and concept of the invention will be more readily understood by reference to the claims, which follow.

The invention claimed is:

1. A backbone cyclic peptide having a structure according to Formula III:

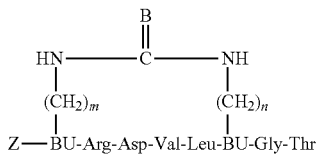

Formula III wherein m and n are each independently an integer of 2, 3, 4 or 6; B is selected from the group consisting of: O, S and NH; Z is selected from the group consisting of: hydrogen, Trp residue, and permeability enhancing moiety; and BU designates a $N^\alpha$-ω-functionalized amino acid residue.

2. The backbone cyclic peptide of claim 1 wherein m is 4 and n is 4.

3. The backbone cyclic peptide of claim 1 wherein BU designates a $N_\alpha$-ω-functionalized Glycine (Gly) residue.

4. The backbone cyclic peptide of claim 1 wherein Z is a Trp residue, a fatty acid or $(DArg)_9$.

5. The backbone cyclic peptide of claim 1 having a structure according to Formula IV:

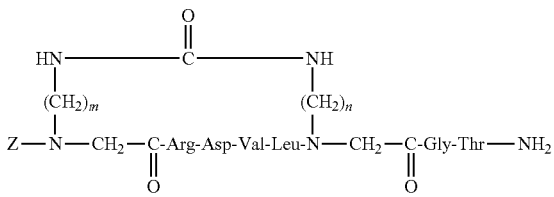

Formula IV wherein m and n each independently designates an integer selected from the group consisting of 2, 3, 4 and 6; and Z is selected from the group consisting of: an hydrogen, an aromatic amino acid residue, a fatty acid residue or $(DArg)_9$.

6. The backbone cyclic peptide of claim 1 wherein n=4, m=4 and Z is selected from the group consisting of: an hydrogen, a Tryptophan (Trp) residue, a myristic acid residue and $(DArg)_9$.

7. The backbone cyclic peptide of claim 1 wherein n=4, m=4 and Z is Trp.

8. The backbone cyclic peptide of claim 1 having a structure according to Formula V:

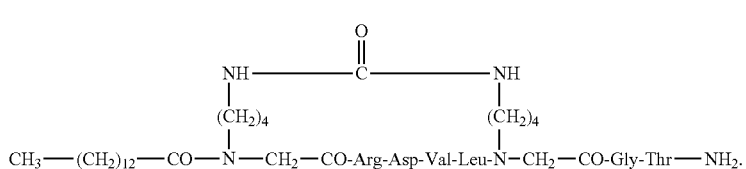

Formula V

9. The backbone cyclic peptide of claim 1 having a structure according to Formula VI:

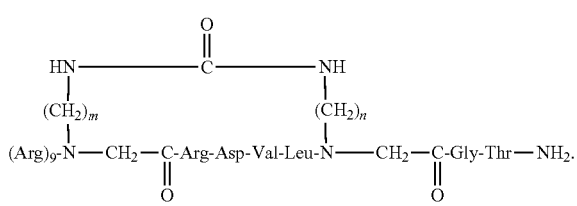

Formula VI

* * * * *